(12) United States Patent
Jenison et al.

(10) Patent No.: US 9,359,637 B2
(45) Date of Patent: *Jun. 7, 2016

(54) METHODS AND COMPOSITIONS FOR AMPLIFYING A DETECTABLE SIGNAL

(71) Applicant: Great Basin Scientific, Inc., Salt Lake City, UT (US)

(72) Inventors: Robert D. Jenison, Boulder, CO (US); Joshua Klonoski, Longmont, CO (US); Anthony R. Torres, Centerville, UT (US)

(73) Assignee: Great Basin Scientific, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/949,240

(22) Filed: Nov. 23, 2015

(65) Prior Publication Data

US 2016/0076080 A1 Mar. 17, 2016

Related U.S. Application Data

(63) Continuation of application No. 14/045,441, filed on Oct. 3, 2013, now Pat. No. 9,200,312, which is a continuation of application No. 12/745,130, filed as application No. PCT/US2008/084790 on Nov. 26, 2008, now Pat. No. 8,574,833.

(60) Provisional application No. 60/990,755, filed on Nov. 28, 2007.

(51) Int. Cl.
*C12Q 1/68* (2006.01)
*G01N 33/543* (2006.01)
*C07H 21/02* (2006.01)

(52) U.S. Cl.
CPC .............. *C12Q 1/682* (2013.01); *C12Q 1/6804* (2013.01); *G01N 33/54306* (2013.01); *Y10T 436/143333* (2015.01)

(58) Field of Classification Search
CPC .......................... C12Q 1/682; C12Q 2527/125
USPC .................................. 435/6.1; 536/23.1, 26.6
See application file for complete search history.

(56) References Cited

U.S. PATENT DOCUMENTS

| 5,695,936 | A | 12/1997 | Mandrand et al. |
| 5,853,993 | A | 12/1998 | Dellinger et al. |
| 6,072,043 | A | 6/2000 | Nilsen |
| 6,103,474 | A | 8/2000 | Dellinger et al. |
| 6,803,196 | B1 | 10/2004 | Lyon et al. |
| 8,574,833 | B2 | 11/2013 | Jenison et al. |
| 9,200,312 | B2 * | 12/2015 | Jenison ................. C12Q 1/682 |
| 2006/0094042 | A1 | 5/2006 | Mackintosh et al. |

FOREIGN PATENT DOCUMENTS

| EP | 0 151 492 A2 | 8/1985 |
| EP | 0 330 221 A2 | 8/1989 |
| EP | 0 783 000 A2 | 7/1997 |
| EP | 1 489 422 A2 | 12/2004 |
| WO | WO 2009/070640 A2 | 6/2009 |
| WO | WO 2009/070742 A2 | 6/2009 |

OTHER PUBLICATIONS

Böcher, Michael, et al., "Synthesis of mono- and bifunctional peptide-dextran conjugates for the immobilization of peptide antigens on ELISA plates: properties and application," *Journal of Immunological Methods* 208:191-202 (1997).
Brakel, C. L., "Antibody-Enhanced Microplate Hybridization Assays", *Biotechniques*, 22(2):346-348, XP000685881 (Feb. 1, 1997).
Dhawan, Subhash, "Design and construction of novel molecular conjugates for signal amplification (II): use of multivalent polystyrene microparticles and lysine peptide chains to generate immunoglobulin—horseradish peroxidase conjugates," *Peptides* 23:2099-2110 (2002).
"Fluorescent and Biotinyloated Dextrans" in: "Handbook of Fluorescent Probes and Research Products, Ninth edition", *Molecular Probes*, pp. 581-590, XP002614902 (2002).
International Search Report and Written Opinion, International Application No. PCT/US2008/084790, 11 pages (Jul. 17, 2009).
International Search Report and Written Opinion, International Application No. PCT/US2008/084990, 12 pages (May 27, 2009).
Klonoski, J., et al., "Enhanced detection of staphylococcal genomes in positive blood cultures using a polymeric enzyme complex", *Analytical Biochemistry*, Academic Press Inc, New York, 396(2):284-289, XP026782052 (Jan. 15, 2010).
Pei, Renjun, et al., "Amplification of antigen—antibody interactions based on biotin labeled protein-streptavidin network complex using impedance spectroscopy," *Biosensors & Bioelectronics* 16:355-361 (2001).
Stratagene Catalog 1988, p. 39.
Zhong, Xiao-bo, et al., "Single-nucleotide polymorphism genotyping on optical thin-film biosensor chips," *PNAS* 100(20):11559-11564 (Sep. 30, 2003).

* cited by examiner

*Primary Examiner* — Jezia Riley
(74) *Attorney, Agent, or Firm* — Brinks Gilson & Lione; Ryan L. Marshall

(57) ABSTRACT

Methods and materials are disclosed relating to an improved method for amplifying a signal in a diagnostic assay for a nucleic acid, comprising the steps of providing an amplification polymer bound to a nucleic acid analyte, wherein the amplification polymer comprises a plurality of amine groups; binding amine groups on the amplification polymer with a detectable label complex; and reacting under high salt conditions an acetylating compound with amine groups not bound with a detectable label complex.

22 Claims, No Drawings

US 9,359,637 B2

METHODS AND COMPOSITIONS FOR AMPLIFYING A DETECTABLE SIGNAL

CROSS REFERENCE TO RELATED APPLICATIONS

This application is a continuation of U.S. patent application Ser. No. 14/045,441, filed Oct. 3, 2013, which is a continuation of U.S. patent application Ser. No. 12/745,130, filed on Nov. 1, 2010, now U.S. Pat. No. 8,574,833, issued Nov. 5, 2013, which is a 371 national phase of PCT/US2008/084790, filed Nov. 26, 2008, and claims the benefit under 35 U.S.C. 119(e) of U.S. Provisional Application No. 60/990,755, filed Nov. 28, 2007, the contents of each of which are incorporated herein in their entirety.

TECHNICAL FIELD

The present invention relates generally to methods and compositions for amplifying a detectable signal used to detect the absence or presence of a nucleic acid analyte in a sample.

BACKGROUND

Many diagnostic assays utilize detectable labels to indicate binding events that that are indicative of the presence or absence of a target analyte in a sample. Typical target analytes include proteins, carbohydrates, or nucleic acids. Generally, such diagnostic assays utilize a target-specific capture molecule that is immobilized on a solid substrate. A sample is placed on the solid substrate and the target analyte, if present, binds to a target-specific capture molecule. The surface-bound target analyte may then be directly modified by binding, directly or indirectly, with a detectable label. Alternatively, a second reagent, modified with a detectable label, may bind to the surface immobilized target. The label can be detected directly in the case of radio-labeled or fluorescent labels using devices such as a phosphor-imager or a fluorescence reader, respectively. Alternatively, the label may be indirectly detected, for example, by binding the label with an anti-label/enzyme conjugate that is subsequently contacted with an enzyme substrate to produce a signal that can be detected.

Due to the low frequency of target analytes in some samples, various methods have been developed to enhance the signal of diagnostic assays using indirect methods. For example, U.S. Pat. No. 5,196,306, discloses a method in which a target-specific, surface-immobilized label is reacted with an amplification polymer to multiply the number of binding sites for a detectable label complex, followed by conjugation with an anti-label antibody conjugate, such as horse radish peroxidase ("HRP") that is then exposed to a tyramide/label conjugate. The tyramide is activated by HRP and then reacts with electron rich groups nearby to physically attach a label molecule.

Several nucleic acid specific techniques have also been developed. For example, U.S. Pat. No. 5,124,246 discloses amplification of a signal by creating branched layers of DNA hybridization in a target nucleic acid sequence specific manner. The layers culminate in a branched structure that can hybridize to hundreds of labels. Other approaches, disclosed in U.S. Pat. No. 6,103,474 and U.S. Pat. No. 6,110,682, amplify a signal by targeting homopolymeric regions of a target nucleic acid analyte with multiple-labeled hairpin reporter probes. A method has also been developed that amplifies biotin-dependent signaling events (Zhong et al., PNAS (2003) 100:11559-11564). In this approach, biotinylated probes are immobilized on a surface in a target-dependent manner, and are then contacted with an avidin-biotinylated dextran copolymer, resulting in a 50-100 fold increase in assay sensitivity.

DNA dendrimers have also been used to amplify signals, as disclosed in U.S. Pat. No. 5,175,270, U.S. Pat. No. 5,487,973, and U.S. Pat. No. 6,046,038. DNA dendrimers are large cross-linked structures that can be modified to contain up to several hundred label groups. These labels groups include biotin, HRP, streptavidin ("SA"), and fluorescent molecules, as disclosed in U.S. Pat. No. 6,072,043; U.S. Pat. No. 6,110,687; and U.S. Pat. No. 6,762,292. DNA dendrimer can contain mixtures of molecules as well, such as SA and HRP. The mixture allows for binding of SA to surface-immobilized biotin, for example. This approach multiplies the number of HRP molecules at the surface of each biotin molecule bound and results in amplification of the signal.

Another technique employs the targeting of homopolymeric regions of target DNA with multiply-labeled hairpin reporter probes, as disclosed in U.S. Pat. Nos. 6,103,474; 6,110,682.

A method was recently disclosed that describes the amplification of biotin-dependent signaling events (Zhong et al., PNAS (2003) 100:11559-11564). Biotinylated probes that were immobilized onto a surface in a target-dependent manner were contacted with an avidin-biotinylated dextran copolymer. This was reported to increase assay sensitivity 50-100 fold increase in assay sensitivity for detection of biotin DNA probes covalently immobilized onto a chip surface. However, it has been observed that this method suffers from some inconsistency and high levels of non-specific interaction between the avidin-biotinylated dextran copolymer and the surface immobilized DNA probesresulting in an improvement in assay sensitivity of only 5-25 fold.

There continues to be a need for improvement in assays for detecting target nucleic acid analytes that may be present in samples.

SUMMARY OF INVENTION

The present invention provides improvements in diagnostic assays for detecting and/or quantitating nucleic acid analytes in a sample. The invention provides improved methods and compositions for amplifying a detectable signal used to indicate the presence or absence of an analyte in the sample. In particular embodiments, the methods and compositions of the invention reduce non-specific interactions that inhibit or interfere with a signal. The present invention provides reagents and methods for improving the sensitivity of a signal generated by means of a plurality of amplification polymers.

In one aspect, methods are disclosed for amplifying a signal in a diagnostic assay for a nucleic acid, comprising the steps of:

(a) providing an amplification polymer bound to a nucleic acid analyte, wherein the amplification polymer comprises a plurality of reactive amine groups;

(b) binding amine groups on the amplification polymer with a detectable label complex; and (c) reacting under an acetylating compound with amine groups not bound with a detectable label complex.

(d) performing test in a salt solution having an ionic strength greater than about 0.5M.

The salt may be monovalent. In some embodiments, the salt may be selected from the group consisting of NaCl and LiCl.

In some embodiments, at least some of the plurality of amplification compounds are not bound to a detectable label complex, and the plurality of amplification polymers not bound to a detectable label are reacted with the capping compound.

In some embodiments, the amplification polymer is selected from the group consisting of multi-valent proteins, dimerized proteins, dimerized antibodies, multimerized proteins, multimerized antibodies, and allosteric aptamers.

The amplification polymers may be comprised of functional binding groups selected from the group consisting of amines, carboxylates, sulthydryls, arginines, maleimides, or aldehydes. For example, the amplification polymer may be selected from the group consisting of the following polymers: dextran, acrylic acid, poly (acrylamide-co-acrylic acid), poly-L-lysine, poly-L-aspartic acid, poly-benzyl-L-glutamate, poly-benzyl-L-aspartate, poly (Arg,Trp), poly (Lys,Phe), polymaleimide and poly-L-glutamic acid. In particular embodiments, the amplification polymer is a dextran polymer, an acrylic acid polymer, or a poly-L-lysine polymer.

In other embodiments, the molecular weight of the amplification polymer ranges from between about 6,000 to about 1,000,000, or alternatively from between about 70,000 to about 500,000.

In order to indicate the presence or absence of a target molecule, the amplification polymer is conjugated to a target analyte.

In other embodiments, the capping compounds use in the methods of the invention will not displace the detectable label complex. In some embodiments, the capping compound may be a stronger base than the functional binding groups to which it binds. For example, the capping compound may be an amine-reactive compound, such as a compound that converts the functional binding groups into amides or imides. By way of example, the capping compound may be an acetylating reagent. Amine-reactive compounds may include compounds from one or more of the following chemical classes: N-hydroxysuccinimidyl (NHS) esters, imidoesters, aryl halides, acyl halides, isocyanates, isothiocyanates, nitrophenyl esters, carbonyls, carboxylates, and acid anhydrides. Particular amine-reactive compounds may include, for example, any one or more compounds selected from the group consisting of NHS acetate, disuccinimidyl suberate (DSS), succinimidyl-3-(tri-N-butylstannyl) benzoate, methyl N-succinimidyladipate (MSA), mono(latosylamido) mono(succinimidyl)suberate, acetic anhydride, aryl chlorides, acyl chlorides, 2,4-dinitrofluorobenzene (DFNB), sulfonyl halides, aldehydes, 1-ethyl-3-(3-dimethylaminopropyl)-carbodimide (EDC) based activation chemistries, maleic anhydride, succinic anhydride, acetyl chlorides, benzoyl chlorides, propionyl chlorides, butyryl chlorides, and penylethanoyl chlorides. The capping compound may also be selected from non-acetylating agents, such as diazoacetates, imidoesters, carbodimides, maleimides, α-haloacetyls, aryl halides, dicarbonyl compounds, sulfhydryls, and hydrazides. By way of example, specific non-acetylating compounds may be selected from the group consisting of, for example, N-ethylmaleimide, N-β-maleimidopropionic acid, N-ϵ-maleimidocaprioic acid, iodoacetic acid, N-[iodoethyl](trifluoroacetamide), 3,4-difluoronitrobenzene (DFNB), sulfonyl halide, (ammonium 4-chloro-7-sulfobenzo-furazan)-chloride (SBF-chloride), glyoxal, phenyglyoxal, 2,3-butanedione, 1,2-cyclohexanedione, 2-mercaptoethanol, dithiothreitol (DTT) followed by sulfhydryl chemistries, (2,4,6-trinitrobenzene sulfonic acid (TNBSA), and 2-mercaptoethanol. The capping compound may also contain a detectable label.

The methods and compositions disclosed herein contemplate the use of a detectable label that is conjugated directly or indirectly to the analyte of interest. Detectable labels may be selected from the group consisting of biotin, fluorochromes, di-nitro-phenol, and digoxigenin. The detectable label may be structurally integrated with a complex that is conjugated to the analyte of interest, or may be a product of the complex. The detectable label complex may comprise, for example, biotin molecules to which are conjugated streptavidin and other molecules capable of being used to generate a detectable signal.

In another aspect, the methods and compositions of the invention may further comprise the step of combining the amplification complex or label with one or more solvating compounds in order to increase the number of amplification polymers that form a complex with the detectable labels.

DETAILED DESCRIPTION

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose, and are understood to represent methods and materials generally known to those skilled in the art.

As utilized in the present disclosure, the following terms, unless otherwise indicated, shall be understood to have the following meanings:

"Acetylating compound" means a compound that reacts with amine groups on the amplification polymer under high salt conditions to acetylate the amine groups not bound with a detectable label complex.

"Amplification polymer" means a polymeric compound that specifically binds, either directly or indirectly, to a target nucleic acid analyte and has a plurality of other binding sites that multiplies the number of detectable labels that can be bound to each target nucleic acid analyte. For example, as described in more detail below, in some embodiments of the invention the amplification polymer may comprise a polymer having a plurality of reactive amine groups to which biotin molecules can be covalently attached. The biotin molecules, when bound to the amplification polymer, can then be used as a binding substrate for a detectable label complex that generates a detectable signal. Because each biotin molecule generates an independent signal, there are multiple signals generated relative to a single analyte to which the polymer binds, thereby amplifying the signal of each analyte.

"Analyte" means a molecule, macromolecule, or compound that is the target of an assay. Although "analyte" is often used in the singular in this application, it should be understood that most samples consist of millions or billions of the identical analyte. Examples of analytes include, but are not limited to, proteins or polypeptide molecules, polynucleotide molecules, organic or inorganic compounds, DNA, polymorphisms of DNA, and RNA.

"Analyte-specific" means that a compound binds specifically, though not necessarily exclusively, to the analyte in a sample.

"Binds" means the formation of an attractive force between two molecules, which includes ionic bonds, covalent bonds, polar covalent bonds, or noncovalent bonds.

"Capture molecule" means a label comprising a functional binding group that binds covalently or non-covalently to the analyte, and further comprising a second functional binding group that binds covalently or non-covalently to an amplification polymer or secondary amplification polymer functional binding group.

"Conjugate" or "complex" means one or more molecules covalently or non-covalently coupled together.

"Detectable label" means a chemical compound that can be either directly or indirectly detected by visual or instrumental means. A detectable label may consist of a molecule that itself produces a signal that can be detected, such as a fluorescent, chemiluminescent or radioactive signal. Alternatively, the signaling label may comprise a molecule that requires reaction with another molecule to generate a signal that can be detected. Detectable labels also include compounds that can be detected visually, for example, colored dyes.

"Detectable label complex" means one or more molecules associated together that enable visual or instrumental detection of a detectable label.

"Label" means, in its generic sense, a molecule or binding site of a molecule that is capable of binding either covalently or non-covalently to other molecules, and being used itself as a binding substrate for another molecule or as a signal for detection. Labels often have different chemical functional groups that react with other chemical functional groups on other molecules. A label can also have multiple functions, for example a capture label could also be a signaling label. Labels may be, for example, an enzyme, antibody, or protein. Labels may also be detectable labels that are used to generate a signal that can be detected for purposes of indicating the presence or absence of an analyte of interest in a sample.

"Signal" means a property or characteristic of a detectable label that permits it to be visually or instrumentally detected and/or distinguished. Typical signals include fluorescent signals, dyes, radioactive signals, etc.

"Specifically binds" means that a compound binds specifically, though not necessarily exclusively, to the analyte in a sample.

The practice of the present invention will employ, unless otherwise indicated, conventional techniques of molecular biology, microbiology, recombinant DNA techniques, and oligonucleotide synthesis which are within the skill of the art. The foregoing techniques and procedures are generally performed according to conventional methods well known to one skilled in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.), the contents of all of which are incorporated herein by reference. Enzymatic reactions and purification techniques are performed according to manufacturer's specifications or as commonly accomplished in the art or as described herein. The nomenclatures utilized in connection with, and the laboratory procedures and techniques of biochemistry, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and diagnosis of patients.

It is to be understood that the foregoing descriptions of embodiments of the present invention are exemplary and explanatory only, are not restrictive of the invention, as claimed, and merely illustrate various embodiments of the invention. It will be appreciated that other particular embodiments consistent with the principles described in the specification but not expressly disclosed may fall within the scope of the claims. Various aspects and embodiments of the methods and compositions of the invention are described in further detail in the following subsections.

The present invention relates to improved methods and compositions for detection of analytes. Improved methods and reagents are disclosed for detection, quantification, and characterization of analytes, such as proteins, carbohydrates, nucleic acids, or other molecules, in a sample. Clinically useful diagnostic methods must be capable of detecting and/or quantifying the presence of an analyte of interest that is present in extremely small quantities in a complex mixture containing similar species. Methods for such diagnostic assays have previously used detectable labels, such as radiolabeling, radiobioassay and immunoassay techniques. For example, immunological reagents have been used extensively for detecting and/or quantitating a broad spectrum of molecular species such as proteins, lipids, carbohydrates, steroids, nucleic acids, drugs, carcinogens, antibiotics, inorganic salts etc. Polyvalent and monoclonal antibodies are very important diagnostic tools in most areas of clinical medicine today.

The methods and compositions of the present invention improve upon methods of the prior art by amplifying the signal generated by an analyte-specific detection complex. In particular embodiments, the improved methods disclosed herein increase the number of amplification polymers available for reaction with a detectable label. In many diagnostic assays, a capture molecule that can recognize specific regions of a target analyte interest is bound to a solid surface and used to capture and immobilize the target analyte on the solid surface. The target analyte bound to the solid surface may then be directly or indirectly modified with a detectable label. The target analyte may be directly labeled with a detectable label, such as a radio-label or fluorescent label. Alternatively, the target analyte may be indirectly labeled, for example, using an anti-label/enzyme conjugate which is then contacted with an enzyme substrate to produce a signal that can be detected. A significant advantage of indirect detection is that intermediate molecules can be conjugated to the target analyte to amplify the number of signals per target analyte bound to the capture molecule. The present invention provides improved methods for signal amplification that reduce interference caused by non-specific binding of amplification polymers.

In a particular embodiment, the present invention relates to methods for detecting an analyte, such as a DNA polymorphism, in a sample. An analyte-specific capture label is conjugated to an amplification complex, which comprises a plurality of amplification polymers that are on a polymer or other macromolecule. Amplification polymers are also known in the art as "binding sites." Each polymer or macromolecule has a plurality of amplification polymers, such as amine groups or other functional binding groups. A detectable label complex is bound to one of the amplification polymers, which can then be detected. Amplification polymer complexes may be, such as biotin, will bind to substantially all of the available amine groups on the polymer or macromolecule. The detectable label will then either directly or indirectly produce a signal that can be detected. In accordance with the methods of the present invention, the unbound amplification polymers are bound with a capping compound to reduce non-specific binding of the amplification complex. The detectable labels are then bound to the to which an analyte is conjugated are separated from the detection labels to which an analyte is not conjugated. If the detectable labels are detected, then the presence of the analyte is inferred. In one embodiment of the invention the unbound amplification polymers are amine groups on a polymer. The capping compound could be an acylating compound that interacts with the amino group and converts it into an acetyl group, which is more stable and less likely to nonspecifically bind to other molecules in the assay.

The methods of the invention provide a novel approach to amplification of a detectable signal conjugated to a nucleic acid analyte. In particular, the invention provides methods for amplification of a detectable signal conjugated to a nucleic acid analyte in high salt concentrations typically used in nucleic acid diagnostic assays. In some embodiments of the invention, the amine groups of the amplification polymer are reacted with an acetylating compound in a salt solution under conditions of ionic strength greater than about 0.5M, to produce an amide group. The capping of the amine group by acetylation provides a neutrally charged, water soluble complex. Salt solutions compatible with nucleic acid detection are well-known to those in the art. In some embodiments, the salt solution comprises a salt that is monovalent. In other embodiments, the salt is selected from the group consisting of NaCl and LiCl.

In particular embodiments, the improved methods comprise the step of reacting the amplification polymers with a capping compound that specifically binds the amplification polymers with greater affinity than the detectable label complex. In other embodiments, the improved methods further comprise the step of combining the amplification polymer with a solvating compound.

Solid Supports

In some embodiments, the methods of the present invention may be practiced by first capturing an analyte of interest on a solid support. In such embodiments, a capture molecule that specifically or selectively binds the analyte of interest is first attached to a solid support. The present invention can also be practiced with or without a solid support. Without a solid support, for example, a capture label binds to the analyte and an electrophoretic separator can be used to separate bound analyte from unbound analyte. However, use of a solid support, such as a chip, may be more cost-effective and accurate.

Solid supports include any material that can be used to immobilize an analyte-specific capture label for use in diagnostic tests and in separation procedures. Natural or synthesized materials, which have or have not been modified chemically, can be used as the solid support, in particular polysaccharides such as cellulose-based materials, for example paper, cellulose derivatives such as cellulose acetate and nitrocellulose, dextran; polymers such as vinyl polychlorides, polyethylenes, polystyrenes, polyacrylates, polyamides, or copolymers based on aromatic vinyl monomers, alkyl esters of alpha-beta unsaturated acids, esters of unsaturated carboxylic acids, vinylidene chloride, dienes or compounds exhibiting nitrile functions (acrylonitrile); polymers of vinyl chloride and propylene; polymers of vinyl chloride and vinyl acetate; copolymers based on styrenes or substituted derivatives of styrene; natural fibers such as cotton and synthetic fibers such as nylon; inorganic materials such as silica, glass, ceramic and quartz; latexes, that is, an aqueous colloid dispersion of any polymer insoluble in water; magnetic particles; metallic derivatives. The solid support according to the invention can be, in the forms which are customarily suitable, for example, in the form of a chip, microchip, microtitration plate, a sheet, a cone, a tube, a well, beads, particles or the like. The choice of a support material can be made, in each particular case, on the basis of simple routine experiments.

Methods are also known in the art for binding to a solid support an oligonucleotide probe for use in detecting specific nucleic acid sequences in a target nucleic acid. For example, oligonucleotides may be immobilized to a solid support by covalent attachment. See, e.g., PCT patent publication Nos. WO 89/10977 and 89/11548. See Chee et al., U.S. Pat. No. 5,837,832. See Strategies for Attaching Oligonucleotides to Solid Supports, Eric J. Devor and Mark A. Behlke, Integrated DNA Technologies (2005). The present invention can be used with all of the above methods.

Analyte-Specific Detection Complex

In one aspect, the present invention provides novel complexes for amplifying a signal in a diagnostic assay for a nucleic acid analyte. The complexes of the invention may comprise (i) an amplification polymer bound to a nucleic acid analyte, (ii) wherein the amplification polymer comprises a plurality of detectable label complexes bound to amine groups and a plurality of amide groups derived from a reaction of an amine group with an acetylating compound, and wherein the complex is neutrally charged and water soluble.

In accordance with the methods of the invention, an analyte of interest is bound to a detection complex that specifically binds to the analyte. Appropriate analytes include any substance for which there exists an analyte-specific binding molecule that can be chemically conjugated to other compounds typically used in chemical or biological assays. The analyte-specific detection complex may comprise may be a protein or polypeptide molecule, a carbohydrate, a polynucleotide molecule, or an organic or inorganic compound. For example, the capture label may be an antibody, a lectin, a DNA repressor protein, a stereospecific receptor-protein, a high affinity enzyme, a sequence specific polynucleotide binding protein, avidin, streptavidin, a hormone or a complementary polynucleotide sequence. Target molecules may be any inorganic or organic species that is capable of producing an affinity with a detecting agent. Other examples of analytes that have been disclosed in the prior art are: proteins, lipids, carbohydrates, phospholipids, fats, nucleotides, nucleosides, nucleoside bases, polynucleotides, polypeptides, cancerogenic agents, drugs, antibiotics, pharmaceutical agents, controlled substances, polymers, silicones, organometallic compounds, heavy metals, metal-protein complexes, toxic inorganic salts, and other agents or compounds produced by or having an effect upon a biological organism or material derived from such molecules. The present invention could be used with any of the examples from the prior art.

The detection complex may include an analyte-specific molecule, such as an antibody, a lectin, a DNA repressor protein, a stereospecific receptor-protein, a high affinity enzyme, a sequence specific polynucleotide binding protein, avidin, streptavidin, a hormone, a complementary polynucleotide sequence, or some other molecule.

Capture molecules may include, for example, proteins (such as receptor molecules or ligands that bind to a specific cognate molecule), oligonucleotides that specifically hybridize to a complementary polynucleotide sequence, or any other molecule known to bind to a cognate molecule with a high degree of specificity. Methods for attaching capture molecules to a solid support are well-known to those skilled in the art, and can be readily selected, as appropriate. See, e.g., *Strategies for Attaching Oligonucleotides to Solid Supports*, Eric J. Devor and Mark A. Behlke, Integrated DNA Technologies (2005).

An especially preferred method for detection of target molecules is based upon the foregoing preferred arrangement, but includes a second bridging component. The complex, i.e., avidin or streptavidin-(biotin ligand)-visualization polymer, is used to complex with a biotin labeled second antibody. The second antibody is a general reagent for the first antibody detecting agent which in turn is specific for the target. The first antibody is incubated with the target to form an antigen-antibody conjugate. Then the second antibody is incubated with this conjugate. Following the second incubation, the amplification molecule is added which binds to the second antibody and enables detection.

Yet another method, according to the invention, also utilizes the indirect complexing ligand arrangement. In this arrangement, the detecting agent is a complementary polynucleotide sequence and the target is the corresponding native polynucleotide sequence which will hybridize with the complementary sequence. The detecting agent and the visualization polymer are labeled with a biotin or iminobiotin group. A complex of avidin or streptavidin-(biotin ligand)-amplification molecule is formed. The labeled polynucleotide detecting agent is added to the complex biological mixture containing the native polynucleotide sequence to be detected. Hybridization is allowed to take place, then the complex is added which binds to the hybridized and labeled polynucleotide detecting agent and which provides visualization.

Amplification Molecules

The methods of the invention further contemplate the use of an amplification molecule conjugated to the target analyte of interest. The amplification molecule comprises a plurality of amplification polymers. Amplification polymers perform the function of providing, for each analyte, multiple bindings sites for a detectable label. Because each analyte is conjugated to multiple binding sites to which a detectable label can be bound, rather than just one binding site for each analyte, the signal associated with each analyte is multiplied or amplified. Amplification polymers are typically in the form of macro-molecules, such as polymers, that have multiple binding groups to which other molecules or complexes can bind and be used as a binding substrate for a detectable label or some other signal.

For example, amplification polymers may be comprised of a biotinylated biomolecule such as an enzyme or protein. Numerous biotinylated biomolecules are known and available to those skilled in the art. Nonlimiting examples of biotinylated biomolecules include biotinylated lectins, antibodies, mitogens, DNA, RNA, tRNA, rRNA fragments, nucleosomes, membranes, membrane proteins, glycoproteins, synthetic peptides.

The polymer or other macromolecule used in the amplification complex can come in many different forms. For example, in the prior art, the reactive chemical groups or backbone moieties of polymer subunits have been used to link the detectable label to the polymer or other macromolecule. For example, if the unit was a protein and was found to contain a dipeptide side chain ending with cysteine, the mercaptan group of the cysteine was cross-linked to cysteine of another similar protein by reaction with bis (N-butylenylmaleimide). The groups and moieties identified may include amine groups, mercaptan groups, carboxyl groups, hydroxyl groups, sugar groups, carbohydrate groups, ester groups, lipid groups, and amide bonds, labile carbon-carbon bonds and carbon-hydrogen bonds. Other measurements such as the relation of derivatization and site activity, relation of pH and site activity and type of site reaction produced in the case of an enzyme will help determine a priority for the functional groups based upon the probability of their presence within the vicinity of the active site. A typical ranking of priority would be: 1) an epsilon or primary amine group, 2) a sugar group, 3) a carboxyl group, 4) a mercaptan group, 5) a hydroxyl group, and 6) a lipid group. If derivatization of amine groups such as those of lysine residues produces a derivatized product devoid of site activity, then the foregoing priority will change and the amine group will be last. The present invention could be used with each of the preceding functional groups.

Tagged natural or synthetic polypeptide, polyol, polyolefin or carbohydrate have had amplification polymers which are substantially less sensitive to the chemical group/backbone moiety bonding arrangement. The fluorescent group, dye, luminescent group, radioactive group or electron dense group which acts as the tag typically have not been subject to variations in activity when adjacent chemical groups or backbone moieties are directly bonded or indirectly linked with coupling agent. Moreover, the prior art has shown that if the tag is to be converted to an active group after the polymer-analyte conjugation is made, then the position of the chemical group or backbone moiety linkage should not interfere with the conversion. Each of these teachings can be applied to the present invention.

The amplification complex will be conjugated to multiple detectable labels, either directly interbonded or cross-linked by a coupling agent. The structural and functional character of the polymer will be similar to that of the monomer units. The number of units per polymer will depend upon the extent of coupling, the stability of the resulting polymer, the reactivity of the chemical groups or backbone moieties relative to the polymer chain length and the position of the groups or moieties along the unit backbone.

Generally, the number of units incorporated into the polymer may vary from as few as two to thousands per polymer. Higher multiples have been possible when the polymer chain length is not of an order which will render the polymer extremely insoluble in aqueous solution or will be extremely susceptible toward mechanical cleavage. The present invention can be used in a similar fashion.

The polymer may be linear or it may be branched. There may be single or multiple coupling between two adjacent units. Coupling may occur at any point along the unit chain so that adjacent units may lie end to end, or may partially or fully overlap. As a result, the three dimensional structure of the polymer may have all of these features. It may be linear, but more typically, it will be a combination of linear and branching units. Partial overlap will typically occur and multiple coupling will also be present.

The accessibility of the chemical groups or backbone moieties has also been shown to affect polymer length. If they are buried within the unit structure, steric inhibition will tend to hinder coupling of a high number of units. This effect may be compensated by use of coupling agents having a chain length greater than about ten carbons in length. Coupling readily accessible groups or moieties with agents which will hold apart the units of the polymer has at times proved advantageous. This has allowed for the facile approach of substrate or reactant and has prevented adverse interaction among the units of the polymer. Typically, agents having a carbon chain length of from about 4 to about 20 carbons have been preferred. The present invention contemplates being used in conjunction with all of the aforementioned methods in the prior art.

The coupling agent linking units together generally is derived from a bifunctional or multifunctional organic cross-linking reagent. In this context, the term coupling agent has indicated the group in its coupled form with a chemical group or backbone moiety. The term cross-linking reagent has been used to indicate the chemical form of the agent before it is reacted with a chemical group or backbone moiety.

The choice of the coupling agent/cross-linking reagent has depended upon the choice of the reactive chemical group or backbone moiety to be coupled and the agent chain length which would avoid intraunit interference within the polymer. See "Reagents For Organic Synthesis", L. Fiezer, M. Fiezer, Vol. 1-8, Wiley & Son; "Cross Linking Reagents" (1980 Ed.), Pierce Biochemical Reagent Catalog, Pierce Chemical Co., Rockford Ill. and references therein, or "Advanced Organic Chemistry" J. March, McGraw Hill (1968).

The amplification molecules and complexes of the present invention detect and chemically amplify the presence of minute quantities of inorganic or organic target molecules which may be found in biological material. Generally, the detection is based upon interaction between the polymer, its complex and the target molecule to be detected. The polymer is carried in a complex carrying arrangement which can bind with specific target molecules and exclude others. Quantitative determination of the target is made by measuring the amount of polymer present in the association formed between the target molecule and carrying arrangement. Signal amplification is provided by the multiple units in the polymer in each association.

The units of the polymer are an important feature providing visualization of the target carrying arrangement association. The units can contain visualization tags or can react with a substrate which can be utilized as a means for quantitative measurement. This measurement may be accomplished by production of a readily identifiable substrate product or production of a spectroscopic signal, as well as other, similar types of nondestructive quantitative analytic methods for measurement. Preferably, the visualization will be based upon the production of color, fluorescence, luminescence, radioactivity, high electron density as well as other forms of spectroscopic measurements.

When the units are enzymes they can generate products which are capable of producing such spectroscopic measurement. For example, they may catalyze reaction of substrates to produce colored, fluorescent, luminescent, electron dense or radioactive products.

Alternatively, the tagged units may be directly utilized as tools for spectroscopic measurement. For example, the natural or synthetic polypeptides, polyols, polyolefins or carbohydrates may be tagged with chemical groups which have coloration, fluorescent, luminescent, electron dense or radioactive properties. These may then be used for spectroscopic measurement.

Enzymes and tagged polypeptides, polyols, polyolefins or carbohydrates possessing the foregoing properties are well-known as means for spectroscopic quantification. When placed in an appropriate spectrometer, the enzymatic substrate or tag will cause a spectrographic change which will indicate the quantity of target present. This process is commonly referred to as visualization and the spectral change is termed the signal produced by the visualization group (the substrate or tag).

The quantity of target to be detected usually will be minute and if the signal from the complex-target association were produced on an equivalent basis, it also would be extremely weak. However, the carrying arrangement and its visualization polymers chemically amplify the signal so that minute quantities of target will produce a strong, readily determined signal. Amplification is achieved by the polymer because it comprises multiple visualization units. The signal provided by each unit is maintained by the polymer. Consequently, its signal is the sum of the signals of its units. In addition, the carrying arrangement may contain multiple numbers of polymer. Although it is not necessary, this multiple arrangement is preferred since it provides further amplification.

The visualization polymer of the invention comprises multiple visualization units monomer directly bonded together or indirectly linked together by a coupling agent bonded to chemical groups or backbone moieties of the units. Each unit also possesses a site or sites which provide the visualization signal. That is it may be a site for enzymatic action or a site to which a visualization tag or tags are attached. The visualization signal activity of the polymer depends upon production of a signal by each unit. Accordingly, the visualization site or sites should be substantially preserved in its or their original form so that the site activity is not substantially decreased. It follows that chemical modification of the units should be conducted in a manner which does not substantially affect the site or sites.

To this end, the direct bonding or coupling agent linkage should join chemical groups or backbone moieties of the units which are at least one atom and in some embodiments at least 3 to 5 atoms away from the visualization site or sites. Also, the choice of chemical groups or backbone moieties for direct bonding or linking with coupling agent should be limited to those which are not present within the site or which are not necessary for site conformation and three dimensional configuration. This choice will be more important for enzyme proteins than for tagged natural or synthetic polypeptides polyols, polyolefins or carbohydrates; however, interference with the production of tag fluorescence, luminescence, coloration, radioactivity or high electron density should also be avoided.

Generally, these site preservation requirements may be met in several ways. If the types of biochemical substructures or chemical residues making up the monomer structure are known, then one which is not part of the visualization site may be chosen as the structure containing the reactive chemical groups or backbone moieties for coupling. Usually, however, a semi-empiric method will be used for choice of the appropriate reactive chemical groups or backbone moieties.

According to the substructure/residue method, the chemical construction of the units will be investigated. The unit backbone substituted groups and functional structures such as sugar groups, lipids, oligomer side chains and the like which are not necessary for visualization site action will be identified. Typically, this would be determined by removal modification or modification of such substructures and study of the activity of the resulting product. Chemical groups or backbone moieties present primarily within these substructures may then be used for direct bonding or indirect linking with the coupling agent. For example, the sugar groups of a glycoprotein which are not necessary for enzymatic activity can be oxidized to dialdehyde groups and reacted with a hydrazine coupling agent to form the visualization polymer.

If the chemical sequence of the unit, such as the amino acid sequence of a protein, can be determined, this may also be utilized to guide direct bonding or indirect linking Analysis of the sequence for the active site as well as the three dimensional configuration will show which unit structural subunits are not essential to functioning of the site and/or not present within it. The reactive chemical groups or backbone moieties of these subunits may be used for bonding or linking with the coupling agent. For example, if the unit is a protein and it is found to contain a dipeptide side chain ending with cysteine, the mercaptan group of the cysteine may be cross-linked to cysteine of another similar protein by reaction with bis (N-butylenylmaleimide).

According to the semi-empiric method, the reactive chemical groups and backbone moieties of the unit can be determined by appropriate spectrographic and chemical analysis. These include techniques such as NMR, IR, chemical derivatization, electrophoresis, osmometry, amino acid analysis, elemental analysis, mass spectrometry and the like. The groups and moieties identified may include amine groups, mercaptan groups, carboxyl groups, hydroxyl groups, sugar groups, carbohydrate groups, ester groups, lipid groups, and amide bonds, labile carbon-carbon bonds and carbon-hydrogen bonds the like [JO needs to clarify this part based on RJ's disclosure]. Other measurements such as the relation of derivatization and site activity, relation of pH and site activity and type of site reaction produced in the case of an enzyme will help determine a priority for the functional groups based upon the probability of their presence within the vicinity of the active site. A typical priority will be 1. an epsilon or primary amine group, 2. sugar group, 3. carboxyl group, 4. mercaptan group, 5. hydroxyl group, 6. lipid group. If derivatization of amine groups such as those of lysine residues produces a derivatized product devoid of site activity, then the foregoing priority will change and the amine group will be last.

Under usual emperic procedures, several versions of polymer will be prepared using a selection of several of the reactive chemical groups or backbone moieties. The activities of the several versions are then tested and the one selected of which has the highest activity. Typically, the selection of chemical groups or backbone moieties will encompass three or four types which are least likely to affect the activity of the visualization site. Each type of reactive chemical group or backbone moiety may eventually be tried if results with the first few are unsatisfactory. Emperic examination of each version of polymer will allow identification of the one with the highest activity.

The units having visualization sites which are very sensitive to the chemical group/backbone moiety bonding arrangement are enzymes. The catalytic site typically will have a conformation closely fitting the substrate and chemical modification which disturbs the three dimensional configuration of the catalytic site may adversely affect the activity of the polymer. Following the foregoing procedures, enzyme site activity can be preserved. Furthermore, the enzyme catalytic site may be protected during bonding or linking by reversibly binding it with substrate.

The units may be any enzyme which will react with an appropriate substrate to produce a colored, fluorescent, luminescent, electron dense or radioactive product. Also, the enzyme may react with a colored, fluorescent or luminescent substrate and quench it. The production or quenching of color, fluorescence or luminescence may result from direct enzyme catalysis or the enzyme may produce an intermediate which enters into a chain of reactions to produce or quench color fluorescence or luminescence.

If an electron dense or radioactive substrate is to be used, the enzyme will act to immobilize it. This may be accomplished by rendering the substrate insoluble, chemically reactive toward the enzyme or otherwise generating an immobilizing physical characteristic. With this type of visualization polymer, the quantity of radioactivity immobilized by the enzymatic reaction or an electron microscopy determination of the quantity of electron dense material present will allow analysis of the minute quantity of target. Examples of such enzymes include peroxidase, alkaline or acidic phosphatase, galactosidase, glucose oxidase, NADPase, luciferase, carboxypeptidase and the like.

The units may also be natural or synthetic polypeptides, polyols, polyolefins or carbohydrates which are tagged. These may be based upon a polyamide backbone, a polyether backbone, a polyvinyl backbone, or poly (sugar) backbone. For the polyamide, the amino acid or diamine compound and dicarboxylic acid compound used to make the backbone may be nonfunctional, i.e., composed of a methylene unit chain ending in the appropriate functional groups, or it may be substituted with groups which would provide side chain functionality. Examples would include glycine, alanine, serine, lysine, aspartic acid and the like as amino acids. Examples of diacids and diamines include arylene or alkylene dicarboxylic acid having at least 6 carbons in the arylene group or 1 to 20 carbons in the alkylene group, and arylene or alkylene diamines having at least 6 carbons in the arylene group and 1 to 20 carbons in the alkylene group. Examples will include poly(3-aminopropionic acid), polyglycine poly(glycyllysine), poly(N-(aminohexyl)alipic amide), poly(N-(aminobutyl)terephthalamide) and the like.

For the polyethers, epoxides and/or oxacyclic compounds with or without hydroxyl substitution can be used as backbone building blocks. Acidic condensation will couple the oxide compounds. Also, the polyols may have a poly(vinyl) backbone with hydroxylic substitution. These may be formed by vinyl/free radical polymerization of alkyl alcohol, butene diol and the like.

For the polyvinyls, vinyl compounds with or without chemical group substitution may be used as backbone building blocks. Vinyl/free radical polymerization of such compounds as acrylamide, acrylic acid, maleic acid, alkyl sulfide, acrylonitrile, methyl acrylate, hydroxyethyl acrylate, alkenyl amine, acrolein, etc. will produce the polyolefin monomers.

For the poly(sugar), glycosidic linking through hemi-ketal condensation of simple sugar building blocks can be used as the carbohydrate backbone formation process. Carbohydrates such as methoxy cellulose, poly(glucose) starch, dextran, polymaltose, amylose, etc. are examples.

The chemical tags include the known, colored, fluorescent, luminescent, radioactive and electron dense probes which will chemically bond with substituents present in a natural or synthetic polypeptides polyols, polyolefins and carbohydrates. These include probes with carboxylic acid derivative substituents, sulfonic acid substituents, imino ester substituents, maleimide substituents, aldehyde substituents, azide substituents and amine substituents which will react with the appropriate functional group of the unit as outlined in Scheme I and Table 1. The probes will be monofunctional rather than difunctional so that they may react only once with a unit chemical group or backbone moiety. Examples of color tags include azido indigo dye, and congo red with sulfonyl chloride substitution. Examples of fluorescent tags include fluorescein with an azido or sulfonyl chloride reactive substituent, 3-azido-(2,7)-naphthalene disulfonate and rhodamine. Examples of radioactive tags include wood reagent (methyl p-hydroxybenzimidate) HCl which can be iodinated, and p-iodobenzenesulfonyl chloride. Examples of electron dense tags include collodial gold, colloidal silver, ferritin, metal binding proteins and reactive lead salts.

Isolation and purification of the visualization polymer of the invention may be accomplished by known techniques used for polymer isolations. These include dialyzation, lyophilization, chromatography, electrophoresis, centrifugation, precipitation by electrolyte adjustment or solvent lipophilicity and the like.

The carrying arrangement of visualization polymer and detecting agent may be direct or indirect. The direct carrying arrangement will have the detecting agent covalently bonded to the visualization polymer by a bifunctional or multifunctional cross-linking reagent. Generally, the bonding will follow Scheme I and method given for linking the visualization units of the polymer. These methods are generally known; for example see K. Peters, et. al., Ann Rev. Biochem., 46, 523-551 (1977); F. Wold, "Methods In Enzymology XXV", pp 623-651 (1972) or M. Das, et al., Ann Rev. Biophys. Bioeng., 8 165-193 (1979). As with the visualization polymer, covalent linkage with chemical groups or backbone moieties of the detecting agent should take place in a region of the agent which will not interfere with its ability to detect the target. This may be determined by any of the methods given above, especially the emperic method.

The indirect carrying arrangement may be of two types. In the first, the detecting agent may be multivalent and have an affinity for the visualization polymer as well as the target. For example, it may be accomplished by employing a multivalent antibody which cross-reacts with the units of the visualization polymer and by utilizing the appropriate amount of antibody and polymer so that at least one of the affinity sites of the antibody remains open. The visualization polymer may also be bonded to a ligand which complexes with a multivalent detecting agent. This will accomplish the same kind of carrying arrangement.

In the second type of indirect carrying arrangement, there will be an intermediate ligand binding compound interspersed between the detecting agent and the visualization polymer. It will display a high affinity for specific ligands and will include an antibody, lectin, avidin, streptavidin, a DNA repressor protein, a high affinity enzyme, a sequence specific polynucleotide binding protein or a complementary polynucleotide sequence. The agent and polymer will be correspondingly labeled with the appropriate ligand. The ligand may be joined to the detecting agent and polymer through a linker similar to a bi or multifunctional cross-linking reagent. Also, the ligand may be substituted for a reactive group of the bi or multifunctional cross-linking reagent.

Alternatively, the ligand may be covalently bonded directly to the detecting agent and polymer. That is, the ligand may be bonded to a chemical group of the polymer and detecting agent which may include an amine group, mercaptan group, carboxylic acid group, hydroxy group, aldehyde group or a C—H group. The procedures and reagents for the appropriate reaction will be chosen depending upon the kind of reactive group present on the ligand.

Methods for the preparation of the carrying arrangements and complexes of the invention follow the well known procedures given in the foregoing background. Examples include use of ligands such as biotin, iminobiotin, polynucleotide sequences, enzyme substrates, sugars, haptens such as 2,4-dinitrophenol, 2,4-dinitrophenylalkylcarboxylic acid having from 1 to 20 carbons in the alkyl group, and carboxylic acid derivatives thereof. Other examples of haptens include 2,4-dinitrophenylalkylamine having from 1 to 20 carbons in the alkyl, phenylarsenate, inistol and trinetrobenzene.

An example of this type of carrying arrangement and complex is based upon use of a complementary strand of polynucleotide as a detecting agent for a specific native polynucleotide sequence. Avidin or streptavidin is used as the ligand binding compound and a functionalized biotin or imino biotin derivative is used as the ligand. Bonding the biotin or imino biotin to the visualization polymer and polynucleotide detecting agent may be accomplished directly or through use of a linker group. These methods are known in the art; see Langer et al., Proc. Nat'l. Acad. Sci. U.S.A., 78, 6633-7 (1981); and follow the methods given for Scheme I except that one end of the bifunctional cross-linking reagent will have been reacted with biotin or iminobiotin. Accordingly, the complex includes avidin or streptavidin-(biotin or iminobiotin ligand)-visualization polymer. The carrying arrangement in addition includes the biotin or imino biotin labeled polynucleotide detecting agent.

The method of the invention utilizing this example can be practiced as follows. An isolated double strand of native polynucleotide to be detected, such as viral DNA, is broken or nicked with a DNAase at random points along each strand. Labeled nucleotide monomers are then translated into the nicks using a polymerase enzyme and the other associated strand as a template. Alternatively, the complementary strands can be directly labeled with biotin label. The labeled complementary pair of polynucleotide strands are then denatured and mixed with a denatured mixture of unknown native polynucleotides, suspected as containing the polynucleotide to be detected. If it is present, hybridization will occur and the labeled double strand may be visualized with the polymer complex.

A second example of a complex is derived from the methods given in the Background for PAP or ABC complex methods or according to Langer et al., supra. In this example, avidin or streptavidin is used as the intermediate ligand, an antibody, lectin, or a sequence specific polynucleotide binding protein is used as the detecting agent and a biotin or imino biotin compound is used as the ligand complexing the visualization polymer and detecting agent with avidin or streptavidin.

In either of these two examples, the biotin or imino biotin compound may be directly coupled with amine or hydroxy groups of the polymer and agent through the use of amide bond or ester bond forming coupling reagents respectively. It may also be coupled through a linker group such as that described above. The linker group is similar to the bifunctional cross-linking reagent except that one of the two reactive groups will be an amine or acylhydrazide group which is coupled with biotin or iminobiotin.

The visualization polymer of the present invention may be used to detect minute quantities of target molecules. These molecules may be found in biological material such as tissue and fluid as well as in artificial or synthetic systems. Examples include blood, lymph, urine, feces, organ tissue such as lung, liver, skin, kidney and the like, microorganisms, plant tissue, cultured cells, hybrid cells, cells with recombinant DNA, synthetic mixtures of polypeptides, immobilized enzyme systems, synthesized DNA and other biological material.

The target molecules may constitute any inorganic or organic species which is capable of producing an affinity with a detecting agent. Preferred targets will be found in the foregoing biological material and systems. Examples include proteins, lipids, carbohydrates, phospholipids, fats, nucleotides, nucleosides, nucleoside bases, polynucleotides, polypeptides, cancerogenic agents, drugs, antibiotics, pharmaceutical agents, controlled substances, polymers, silicones, organometallic compounds, heavy metals, metal-protein complexes, toxic inorganic salts, and other agents or compounds produced by or having an effect upon a biological organism or material derived therefrom.

Generally, the procedures for combination and, incubation of the detecting agents and targets are well known. They follow methods used for affinity and immunodiagnostics assays; see for example L. A. Sternbeyer, "Immunohistochemistry" cited above. For example, combination of metered amounts of agent and target in buffered aqueous solution followed by incubation at temperatures from ambient to about 37° C. for periods such as 5 minutes to 18 hr. will cause conjugation. Addition of the visualization polymer or its complex under similar conditions will then provide visualization. Finally, if the agent is bonded to the visualization polymer, similar techniques can be followed.

Use of the visualization polymer for the foregoing detection purposes has advantage since it allows detection of extremely minute quantities of target molecules. It may be employed in medical diagnostic laboratory as an analytical technique for identification of biological products in fluids and tissues which are indicative of a disease state. These would include for example, abnormal amounts of growth hormone, the presence of human gonadotropin indicating cancer, detection of viral invasion, quantification of hormone and regulatory enzyme levels. Also, it may be employed to perform normal fluid and tissue chemistry analyses and may be employed in the biochemical research laboratory as a tool for identification of biochemical substances.

The visualization polymer may be used in synthetic protein or polynucleotide work to identify synthesized, semisynthetic or native proteins and synthesized, recombinant or native polynucleotides. Applications will be found in the course of preparative or bulk work to produce useful proteins such as insulin, interferon, ACTH, gonadotropin, oxytocin, pituitary hormone, LH, FSH and the like by such techniques as recombinant DNA or hybridomas.

The carrying arrangement of detecting agent and visualization polymer complex will be the form for use to perform the foregoing analyses. Since the polymer will provide multiple signals from the carrying arrangement association with the target, chemical amplification will result. In the preferred form of the carrying arrangement wherein a complex of polymer and ligand binding compound is employed, the signal amplification by the polymer will be further increased by multivalent liganding of multiple numbers of polymer to each molecule of detecting agent. Accordingly, in the preferred embodiments employing an antibody or complementary polynucleotide sequence detecting agent, biotin or immobiotin labels, on the agent and polymer, and an avidin or streptavidin, detection of femtomole ($10^{-15}$) quantities can be achieved. This will also depend in part upon employing a sensitive visualization unit system and the appropriate carbon chain linker lengths for both the biotin labels and the coupling agent of the polymer. An example would be use of the enzymes alkaline phosphatase or horseradish peroxidase coupled as visualization polymer by epsilon amino group bonding with an active diacyl derivative of suberic acid, and use of biotin labels with carbon chain linkers of from 6 to 14 carbon in length.

The polymer, complex and carrying arrangement of the invention may be formulated as an integral part of a solid or liquid detection system and kit. Colorimetric, fluorescent, luminescent and radioactive systems may be prepared in this manner. Such systems and kits would include the detecting components, i.e., the polymer, its complex with a ligand, a ligand binding compound, and the detecting agent as well as the appropriate chemicals, reagents and solutions in metered amounts and standardized concentrations also. For example, if enzymatic action with a substrate to produce a colored product is to be the visualization procedure employing the polymer, the system and kit will contain the chemicals, substrate and reagents necessary for performing this analysis. These materials will be present as metered quantities so that the light absorption produced by the colored product may be used in conjunction with a standard Beer's Law mathematical formula to determine the concentration of target detected. Usually, a standard reaction of polymer with substrate will be employed as a control and reference, although standard graphs of absorption relative to concentration may also be utilized.

Fluorimetric, lumimetric and radiometric analyses may be performed in a similar fashion. The intensity of fluorescence, luminescence or radioactivity produced by the polymer in the carrying arrangement associated with the target will be measured by the appropriate electronic machine Necessary reagents and chemicals will also be present. Metered amounts of components will be employed so that the intensity value may be correlated with the quantity of target using a standard Beer's Law mathematical formula.

In these systems, a concentration of detecting agent-visualization polymer complex will be used in the test solution which is sufficient to associate with all the target to be detected. Preferably, the concentration will provide an excess amount. The target may be grossly separated from other material by sedimentation, by centrifugation, or otherwise separated by such techniques as high pressure liquid chromatography, gel permeation chromatography, electrophoresis, precipitation, thin layer chromatography, paper chromatography or similar techniques. However, this is not necessary for the purposes of this invention. The signal producing reaction will be initiated by forming the target-detecting agent conjugate followed by forming the visualization polymer-detecting agent associative arrangement and measuring the visualization signal from this arrangement. Comparison of the signal intensity with a standard graph will yield the quantity of target. Other techniques such as conjugate-complex exchange, which are known in the field of immunoanalysis, may also be used.

With all of the foregoing liquid and solid analysis methods, qualitative detection may also be made. Since this object will be determination of the presence of the target to be detected rather than quantity, standardization need not be used. The qualitative techniques will generally follow the methods for the foregoing quantitative techniques.

Aptamers

Aptamers have some advantages over antibodies, which may not be able to detect low concentrations of analyte if the binding affinity between an antibody and an analyte are too low. Aptamers have been developed to bind specifically to target molecules for purposes of identifying the molecules for disease analysis. PCT application number WO 99-07724, by Nextar Pharmaceuticals, Inc., authored by Heilig and Gold, "Nucleic Acid Ligands for Blood-Brain and Cerebrospinal Fluid-Blood Barriers by Tissue SELEX," published Feb. 18, 1999, discloses use of the SELEX system of obtaining a nucleic acid that has a sequence capable of binding a target protein with high affinity and specificity, in this case for components of cerebrospinal fluid and the blood-brain barrier. Aptamers have been developed for a variety of different types of target materials. See also, for example, PCT application number WO 95/07364, by Nexagen, Inc., authored by Gold et al., "Nucleic Acid Ligands and Improved Methods for Producing the Same," published Mar. 16, 1995; and PCT application number WO 91/19813, by University of Colorado Foundation, authored by Gold and Tuerk, "Nucleic Acid Ligands," published Dec. 26, 1991. The foregoing publications and the references cited therein are hereby incorporated herein by reference. Aptamers and similar structures of the prior art may also be used in conjunction with the present invention.

Conjugation of Compounds

The capture molecule may be directly conjugated with the amplification complex via direct covalent or non-covalent bonding with the polymer, or indirect bonding through an intermediate covalent or non-covalent binding group. The capture label may also be conjugated to the polymer or other macromolecule through an intermediate ligand binding complex. In a direct binding arrangement, the capture label acts as a ligand binding compound also and the corresponding ligand is bound to the amplification polymer. In an indirect binding arrangement, a first ligand is bound to the agent, a second ligand is bound to the polymer and they are sandwiched with a ligand binding compound such that the first and second ligands function as bridges that form a complex with the compound.

Methods for conjugating the amplification complex are well known in the prior art. Examples include use of ligands such as biotin, iminobiotin, polynucleotide sequences, enzyme substrates, sugars, haptenes such as 2,4-dinitrophenol, 2,4-dinitrophenylalkylcarboxylic acid having from 1 to 20 carbons in the alkyl group, and carboxylic acid derivatives thereof. Other examples of haptenes include 2,4-dinitrophenylalkylamine having from 1 to 20 carbons in the alkyl, phenylarsenate, inistol and trinitrobenzene. All of the foregoing examples can be used with the present invention.

Complementary strands of a polynucleotide have been used as a detecting agent for a specific native polynucleotide sequence. Avidin or streptavidin is used as the ligand binding compound and a functionalized biotin or imino biotin derivative is used as the ligand. Bonding the biotin or imino biotin to the amplification complex may be accomplished directly or through use of a linker group. These methods are known in the art. See Langer et al., Proc. Nat'l. Acad. Sci. U.S.A., 78, 6633-7 (1981). Accordingly, the amplification complex may be composed of an avidin or streptavidin-(biotin or iminobiotin ligand)-polymer.

A biotin or imino biotin compound may be directly coupled with amine or hydroxy groups of the polymer and agent through the use of amide bond or ester bond forming coupling reagents, respectively. It may also be coupled through a linker group such as that described above. The linker group is similar to the bifunctional cross-linking reagent. The present invention could be used with biotin or imino biotin compounds.

Biotinylated Molecules

Examples of the detectable label include, but are not limited to, biotin or any derivatized form or analog thereof, or any molecule having an affinity for avidin including monomeric avidin, streptavidin, or any protein having biotin-binding properties including recombinant forms of any of the above. It should be noted that streptavidin has four binding sites for biotin; thus many examples in the prior art include a biotin-streptavidin-biotin complex. Patents and literature are replete with the various biotin compounds including various spacers, linking groups and the like, for use in the present applications. Nonlimiting examples can be found in M. D. Savage, et al. (1992), Pierce Chemical Co., Avidin-Biotin Chemistry: A Handbook; DE 3629194, U.S. Pat. Nos. 5,180,828, 4,709,037 and 5,252,743, 4,798,795, 4,794,082, WO 85/05638 incorporated herein by reference. For a basic reference on using biotin and horseradish peroxidase signals, see Adams, J. Histochem. Cytochem. 1992 October; 40:1457-63. The prior art discloses a modification of the Adam's protocol wherein biotin amplification was applied to early gene screening and also to enhance the metal portion of diaminobenzidines used in an immunoperoxidase method. Berghorn, et al., J. Histochem. Cytochem., 1994 December; 42: 1635-42. The same or similar method could be used with the present invention.

Amplification Polymers

The presence of a target analyte of interest may be visualized by binding to the target analyte an amplification molecule that amplifies the number of binding sites per target analyte. As used herein, the term "amplification polymer" is used to refer to the binding sites of an amplification molecule. An amplification molecule may comprise, for example, a polymer having multiple binding sites covalently linked together by polymerization or non-covalently coupled together. The amplification molecule binds to the analyte or an intermediate molecule via a binding site on the amplification molecule. Each unit of the polymer is coupled to at least one signal label, and the units are linked in a manner which preserves the intrinsic activity of the binding sites or amplification polymers of the units. An amplification unit can generate or produce color, fluorescence, luminescence, localization of radioactivity or localization of electron dense material. The units may be selected from an enzyme or a tagged natural or synthetic polypeptide, a tagged polyol, tagged polyolefin, or a tagged carbohydrate. Thus, each amplification molecule that binds to an analyte provides multiple additional binding sites (or "amplification polymers") to which a detectable label can be bound, thereby providing amplification of the number of signaling events per target molecule bound to the solid substrate.

The units may be directly linked by polymerization or indirectly linked by a coupling agent. Direct polymerization or agent coupling bonds chemical groups or unit backbone moieties of adjacent units. The chemical groups or backbone moieties utilized for each unit of polymer will be independently selected from an amine group, an oxidized form of a 1,2-diol group, a carboxy group, a mercaptan group, a hydroxy group or a carbon-hydrogen bond. For example, oxidative enzymes such as horseradish peroxidase can be used to polymerize monomer units by oxidative cross-linking.

Alternatively, a coupling agent may be used, which may be derived from a bifunctional or multifunctional organic cross-linking reagent, bonds with the appropriate chemical group or backbone moiety of the units. In this context the term "coupling agent" denotes the linkage group after bonding and the term cross-linking reagent denotes the linkage compound before bonding.

Bound amplification polymers refers to those functional groups on the polymer that bind to the signal labels. Unbound amplification polymers on the amplification polymer, such as a dextran polymer, refers to those functional binding groups that could bind to the signal labels, such as biotin, but remain unbound because under experimental conditions, chemical reactions almost never go completely to completion.

Capping Amine Groups

The finding that capping the unbound functional groups on polymers could lead to an increase in signal was unexpected. Unreacted amine groups are known to bind non-specifically to surfaces or molecules in the assay, and this non-specific interaction interferes with the amplification of the signal. Initially, it was believed that this problem was due to charge interactions with the amine $NH_2+$ ions. Ordinarily, such charge interactions can be reduced by increasing the salt concentration so that there are more negatively charged Cl− ions in solution. However, it was observed that the higher salt concentration did not decrease non-specific binding. Reactive amine groups were then capped, which resulted in amplification of the signal by 100-fold.

Reactive amine groups may be capped using various chemical processes. For example, an iminoester salt reagent may be reacted with an amine chemical group to produces an amidine coupling agent linkage. The reagent may be generated from the acidic alcoholysis of the corresponding nitrile. The amidine formation reaction may be conducted in aqueous or polar organic solvent under mild conditions. The methods and procedures are known. See, e.g., Lockhart, et. al., Can. J. Biochem., 53, 861-867 (1975) and Pierce Biochemical Reagent Catalog and references therein, supra.

Amine groups may also be reacted with an aldehyde reagent to form a bis Schiff base (imine) in a condensation reaction. Examples include glutaraldehyde and other tissue fixing reagents. Conditions include use of polar organic solvent and mild temperatures.

In another embodiment found in the prior art, an aldehyde chemical group is reacted with amine groups and amine derivative reagents to form imine and imine derivative compounds. These reagents and reactions included primary amine reagents and reagents which react to form a Schiff base (imine). In the prior art other embodiments included substituted hydrazine reagents, which react to form substituted hydrazones, and acyl hydrazide reagents, which also react to form acyl hydrazones. The present invention contemplates similar applications.

Other capping chemistry options include maleic anhydride, acetic anhydride, succinic anhydride, N-maleimide derivatives, aryl halides, alkyl halides, aldehyde, ketone derivatives, and chemistries that create carboxylates. Other substituent groups may be useful for capping functional groups.

The following list contains other chemical classes and examples of chemicals from those classes that in theory could be used to cap unbound functional groups: carboxylate reactive chemistries, such as diazoacetate, imidoesters, carbodimides; sulfhydryl reactive chemistries, such as maleimides (N-ethylmaleimide, N-beta-maleimidopropionic acid, N-epsilon-maleimidocaprioic acid), alpha-haloacetyls (iodoacetic acid, N-[iodoethyl]trifluoroacetamide), aryl halides (DFNB, sulfonyl halide, SBF-Chloride); arginine reactive chemistries, such as dicarbonyl compounds (glyoxal, phenyglyoxal, 2,3-butanedione, 1,2-cyclohexanedione); maleimide reactive chemistries, such as sulfhydryl, e.g. 2-mercaptoethanol, DTT followed by sulfhydryl chemistries; fluorescent protecting groups; fluorescent protecting groups, such as sulfhydryls (SBF-chloride), amine (TNBSA); aldehyde reactive chemistries, and hydrazides.

Amine-reactive compounds and compounds that are not amine-reactive may also be used, for example, acetylating reagents, such as NHS-acetate and acetic anhydride. Aldehydes, sulfhydryls, and carboxylates may also be used to cap polymers with free reactive groups other than amine groups. Some chemistries can react with multiple groups. For example free-SH and free-NH2 can show similar reactivities depending on the pH of the solution.

Amine-Reactive Compounds

If there are free, reactive amine groups on the polymer or other macromolecule, they could first be protected with a removable protecting group such as a Schiff base, i.e., condensation of the amine groups with an aromatic aldehyde such as p-methoxybenzaldehyde or benzaldehyde which could be removed with dilute hydrogen chloride in acetone. Other known amine protecting groups may also be used. These include dinitrofluorobenzene, t-butoxy groups and organosilanes.

After protection, esterification can be conducted using an activated acid reagent. Unit residues that have esterified in this fashion have included amino acid residues of serine, threonine, hydroxylysine, tyrosine, thyroxine, hydroxyproline, carbohydrate, starch, lipid and olefinic residues with hydroxyl substitutions, including hexoses, pentoses, dextrans, amyloses, glycerols, fatty acid derivatives, methylhydroxymethacrylate, hydroxymethyl acrylate and similar compounds. The present invention could be used with all of the foregoing examples.

Detectable Label

Preferred detection methods and preferred amplification molecule include polymers having multiple units of an enzyme or multiple units of a natural or synthetic polypeptide or polyolefin chemically bonded to a tag selected from a fluorescent group, a dye, a luminescent group or an electron dense group.

Preferred enzymes include alkaline phosphatase, peroxidase, galactosidase, glucose oxidase, acid phosphatase and luciferase. Preferred polypeptides include polyamides of dicarboxylic acids and diamine, polyamides, oligomers and copolymers of alpha amino acids such as glycine, lysine, aspartic acid, cysteine, ornithine and the like. Polyolefins include polyacylamide, polyacrylic acid, polymaleic acid, poly(hydroxyethylacrylic ester) and the like. These polypeptides and polyolefins will be tagged with such groups as fluorescein, rhodamine, a diazo dye, colloidal gold, luciferin, radioactive iodine and the like.

The detectable labels may be directly utilized as tools for spectroscopic measurement. For example, the natural or synthetic polypeptides, polyols, polyolefins or carbohydrates may be tagged with chemical groups which have coloration, fluorescent, luminescent, electron dense or radioactive properties. These may then be used for spectroscopic measurement.

The detectable labels of the units can be sites of biological activity. For example, sites for enzymatic action will provide visualization when reacted with an appropriate substrate. In this manner, the visualization sites can be utilized to generate soluble or insoluble bodies of color, fluorescence, luminescence, radioactivity or high electron density which can be measured and correlated with the quantity of target molecules detected.

The sites may also be created chemically. Combining a natural or synthetic polypeptide, polyol, polyolefin or carbohydrate with a visualization tag selected from a fluorescent chemical group, a dye, a radioactive group, a photon emitter (a luminescent group) or an electron dense moiety will produce monomer units which can be visualized.

The detectable label will be present at a ratio greater than one unit of detectable label per target analyte. In some embodiments, the detectable label may comprise an enzyme, which may be conjugated to a polymer, such that the number of enzyme molecules conjugated to each polymer molecule is, for instance, 1 to 200, 2 to 50, 2 to 25, or some other ratio. In some embodiments the secondary amplification polymer may be a gold particle, a radioactive isotope, or a color label, e.g. a low molecular weight fluorophore, and the number of detectable labels conjugated to each polymer molecule is, for instance and not by way of limitation, 1 to 500 or 2 to 200. In some embodiments the detectable label may comprise a protein fluorophore. The detectable label and may be detected by numerous methods including reflectance, transmittance, light scatter, optical rotation, and fluorescence or combinations hereof in the case of optical labels or by film, scintillation counting, or phosphorimaging in the case of radioactive labels. See e.g., Larsson, 1998, Immunocytochemistry: Theory and Practice, (CRC Press, Boca Raton, Fla.); Methods in Molecular Biology, vol. 80, 1998, John D. Pound (ed.) (Humana Press, Totowa, N. J.). In some embodiments more than one type of detectable label or more than one detectable label may be employed. The present invention contemplates using all of the aforementioned embodiments.

Isolation and purification of the detectable labels that are conjugated to the analyte may be accomplished by any one of various techniques used for polymer isolation known to those skilled in the art, including dialyzation, lyophilization, chromatography, electrophoresis, centrifugation, precipitation by electrolyte adjustment or solvent lipophilicity and the like.

Detection

A variety of procedures are available to visualize specific antigen-antibody interactions fluorimetrically or colorimetrically. Since the utility of immunodiagnostic procedures often depends upon the sensitivity and the specificity with which the target antigen or molecule can be detected, new methods for increasing these detection parameters are highly desirable. A detailed discussion of the advantages and disadvantages of immunologic methods can be found in any standard textbook on immunocytochemistry. See, for example, L. A. Sternberger, "Immunohistochemistry," 2nd Ed., John Wiley and Sons, New York, 1979.

Detecting the presence of a detectable label often requires that the detection label be conjugated to some type of label that produces a signal. Producing the detectable signal may be performed using any of the methods in the prior art. For example, chemical tags include the known, colored, fluorescent, luminescent, radioactive, and electron dense probes which will chemically bond with substituents present in a natural or synthetic polypeptide or carbohydrate. These include probes with carboxylic acid derivative substituents, sulfonic acid substituents, imino ester substituents, maleimide substituents, aldehyde substituents, azide substituents and amine substituents which will react with the appropriate functional group. Probes may be monofunctional rather than bifunctional so that they may react only once with a unit chemical group or backbone moiety. Examples of color tags include azido indigo dye, and congo red with sulfonyl chloride substitution. Examples of fluorescent tags include fluorescein with an azido or sulfonyl chloride reactive substituent, 3-azido-(2,7)-naphthalene disulfonate and rhodamine. Examples of radioactive tags include wood reagent (methyl p-hydroxybenzimidate) HCl which can be iodinated, and p-iodobenzenesulfonyl chloride. Examples of electron dense tags include colloidal gold, colloidal silver, ferritin, metal binding proteins and reactive lead salts. The present invention is contemplates using the foregoing methods Immunologic detection methods can utilize direct or indirect visualization techniques for measurement of the formed immune complex. In general, these methods visually indicate the presence of the complex through use of an entity coupled to the complex which produces a detectable, quantifiable signal such as color, fluorescence, radioactivity, enzymatic action and the like. The greater the signal intensity present per complex, the better will be the sensitivity for the presence of a minute quantity of target molecule. Enzymes and tagged polypeptides, polyols, polyolefins or carbohydrates are well-known as means for spectroscopic quantification. When placed in an appropriate spectrometer, the enzymatic substrate or tag will cause a spectrographic change which will indicate the quantity of target present.

Of the various methods available in the art, the simplest and least sensitive is direct immunofluorescence. In this method, a primary antibody (or specific ligand-binding protein) is chemically linked to a fluorochrome, such as rhodamine or fluorescein which functions as the signal entity. Indirect immunofluorescence methods, in which a primary antibody is used unmodified and it, in turn, is detected with a fluorescently-labeled secondary antibody, generally will increase the detection sensitivity. An additional three to five-fold enhancement in sensitivity has been reported using a "hap-tene-antibody sandwich" technique. See Cammisuli, et al., J. Immunol., 117,1695 (1976); Wallace, et al., J. Immunol Methods, 25, 283 (1979). According to this technique, ten to fifteen molecules of a small haptene determinant such as 2,4-dinitrophenol are chemically coupled to each primary antibody molecule. Then, by use of a fluorescently-labeled second antibody which complexes with the haptene molecules, rather than with the primary antibody itself, more of the secondary visualization protein can be bound per antigen site, thus further increasing the sensitivity.

Secondary antibodies have been coupled to monomeric horseradish peroxidase and used the catalytic activity of peroxidase enzyme to reveal either the site, or the amount, of antigen in the test sample. See Nakane, et. al., J. Histochem. Cytochem., 22, 1084 (1974); Wilson, et. al. "Immunofluorescence and Related Staining Techniques", W. Knapp, H. Holuban and G. Wick, Eds. Elsevier/North-Holland Biomedical Press, 215. Similar enzymatic assays have been developed with intestinal or bacterial alkaline phosphatase conjugated secondary antibodies. See Avrameas, Immunochemistry, 6, 43, (1969); Mason, et. al., J. Clin. Path., 31, 454 (1978).

The enzymatic signal of this method can occur in at least two ways. Enzymatic conversion of a soluble enzyme substrate into an insoluble, colored product permitted the direct localization of the antigen by direct macroscopic visualization, light microscopic examination, or by using other types of apparatus. Alternatively, colorless substrates were enzymatically converted into soluble colored products which were used to quantitate antigen concentrations by direct colorimetric analysis. The latter method is the basis of the Enzyme-Linked Immuno-Sorbent Assay (ELISA), which has been widely used in clinical laboratories around the world. See Stemberger, Immunohistochemistry, 2d ed., John Wiley and Sons, N.Y. (1979); Engvall, et. al., Immunochem., 8, 871 (1972); Engvall, et al., J. Immunol., 109, 129 (1972); Guesdon, et. al., J. Histochem. and Cytochem., 27, 1131 (1979); Voller et. al., "The Enzyme Linked Immuno Sorbent Assay (ELISA)", Dynatech Laboratories Inc., Alexandria (1979). These enzyme-based detection methods are generally more sensitive than direct or indirect immunofluorescence methods since the high turnover of substrate by the enzyme continuously accumulates a measurable product over long periods of time.

To further increase the sensitivity of immunoenzyme assays, a three stage peroxidase-antiperoxidase (PAP) assay method has been used. See Sternberger, et. al. J. Histochem, Cytochem. 18, 315 (1970). Following the addition of a primary antibody and a secondary antibody, which acts as a bridge between the primary antibody and antiperoxidase antibody, a peroxidase-antiperoxidase antibody complex (PAP complex) is added to the sample prior to the development of the enzymatic reaction. Since the PAP complex contains two immunoglobulins (antiperoxidase antibodies) and three active peroxidase molecules, the net effect is to provide more enzyme at the antigen site with which to amplify the detection signal. Although quite useful, the PAP detection system has limitations. The secondary "bridge" antibody has to be used at saturating levels to ensure optimal binding of the PAP complex. Furthermore, the antiperoxidase and the primary antibody should be of the same, or an immunologically cross-reacting, species so that the secondary antibody will bridge to both. Although the present invention contemplates the use of the foregoing, the present invention also contemplates the use of biotin and streptavidin/avid analogs.

Specific interaction between biotin, a small water soluble vitamin, and avidin, a 68 kDa glycoprotein from egg white, can be exploited to develop antigen or ligand detection systems. See Bayer and Wilchek in Voller, et. al., "The Enzyme Linked Immuno Sorbent Assay (ELISA)", Dynatech Laboratories Inc., Alexandria (1979). Biotin may be covalently conjugated to amino, carboxyl, thiol and hydroxyl groups present in proteins, glycoproteins, polysaccharides, steroids and glycolipids using well established chemical reactions. See Guesdon, et. al., J. Histochem. and Cytochem., 27, 1131 (1979); Stemberger, et. al., J. Histochem. Cytochem., 18, 315 (1970); Bayer, et. al., Methods Biochem. Anal., 26, 1, (1980); Bayer, et. al., J. Histochem. Cytochem., 24, 933 (1976); Heitzmann, et. al., Proc. Natl. Acad. Sci. USA, 71, 3537 (1974). Biotin may also be introduced into other macromolecules, such as DNA, RNA and co-enzymes, by enzymatic methods that utilize biotin-labeled nucleotide precursors. See Langer, et al., Proc. Natl. Acad. Sci. USA, 78, 6633 (1981). Similarly, avidin may be coupled to a host of molecular species by standard chemical reactions. See Stemberger, Immunohistochemistry, 2nd Edition, John Wiley and Sons, N.Y. (1979); Nakane, et. al., J. Histochem. Cytochem., 22, 1084 (1974); Guesdon, et. al., Histochem. and Cytochem., 27, 1131 (1979); Bayer et. al., Methods Biochem. Anal., 26, 1, (1980). This allows for great flexibility in designing detection systems for use in immunology, immunopathology and molecular biology.

Avidin-biotinylated horseradish peroxidase complex (ABC) has also been used for antigen detection. Hsu, et. al., Amer. J. Clin. Path., 75, 734 (1981); Hsu, et al., J. Histochem. Cytochem., 29, 577 (1981). In a three-step procedure, the primary antibody incubation is followed by an incubation period with a biotin-labeled secondary antibody and then with the ABC complex, formed by preincubating avidin with a titrated amount of biotinylated peroxidase. Since avidin has four biotin-binding sites per molecule, at least three peroxidase enzymes can be added to avidin without interfering with its ability to interact with the biotinylated secondary antibody. The ABC detection procedure was reported to be 4-8 times more sensitive in detecting antigens in tissues than either the immunoperoxidase or the PAP detection systems. The ABC method is four-fold more sensitive for antigen detection using an ELISA system than either the immunoperoxidase or the PAP techniques. Madri, et. al., Lab. Invest., 48, 98 (1983).

The sensitivity for the ABC method, however, is limited. Typically, only 30 to 100 pg of a target molecule can be detected. This is significantly higher than the upper limit required for detection of a single molecule per cell. Limits for other less sensitive methods are even higher. Accordingly others have developed visualization methods which substantially improve sensitivity over that provided by known visualization techniques.

Non-Ionic Polymers

The methods of the invention further comprise the step of reacting the amplification polymer and detection complex in the presence of a high molecular weight non-ionic polymer. The non-ionic polymers are useful in increasing the detection sensitivity of the assay by reducing background noise from non-specific binding between amplification complexes, detectable labels nucleic acids, etc. Useful non-ionic polymers include, for example, a dextran sulfate, an amino dextran, a polyvinyl pyrollidone (PVP), a polyvinyl sulfate (PVS), a polyethylene glycol (PEG), a carboxymethyl cellulose, a hyaluronic acid or a polyacrylic acid (PAA), or co-polymers such as poly(acrylic acid-co-maleic acid). Non-ionic polymers are obtainable in differing degrees of polymerisation, i.e. with different molecular weights. For the present invention, high molecular weight non-ionic polymers are preferred, the upper limit of the molecular weight depending upon the molecular weight at which the polymer is no longer sufficiently soluble to be effective according to the present invention. For use in the process according to the present invention, polyethylene glycol has a molecular weight of from about 6 kD to about 300 kD, with a molecular weight of about 40 kD being particularly useful. Polyvinylpyrrolidone is also useful as non-ionic polymer, having a molecular weight of at least about 40 kD, and up to about 100-750 kD. Dextran may be used which has molecular weight of about 200 kD, and up to about 500-1,000 kD. The concentration of the non-ionic polymer may be, for example, from about 0.5 to about 3% by weight, and can be present as powder, lyophilisate or solution.

Kits

In another aspect, the invention provides kits for amplifying a detectable signal. The kits of the present invention may include (i) a capture molecule that specifically binds the nucleic acid analyte; (ii) an amplification polymer adapted to be conjugated to the nucleic acid analyte, wherein the amplification polymer comprises a plurality of amine groups; (iii) a conjugation compound capable of conjugating the amplification polymer to the nucleic acid analyte; (iv) an acetylating compound capable of reaction with amine groups on the amplification polymer to create amide groups; and (v) a detectable label complex.

The invention is illustrated by the following examples. These examples are not limiting and other similar procedures as shown by the examples will be readily apparent to those skilled in the art. All measurements are provided in the metric system unless otherwise noted.

EXAMPLES

Example 1

The following three chips were used: Biotin Chip dil#1, Biotin Chip dil#2, and the MRSA Chip. Chips were purchased from Inverness Medical—Biostar Inc. Surfaces were coated with 5 ug/mL of poly (Lys-Phe) in 1×PBS, 2M NaCl pH 6 overnight. Surfaces were washed with water and then coated with 10 uM SFB in 0.1M Borate buffer pH 8.5 for 2 hours at room temperature. Chips were again washed with water, dried with a stream of nitrogen, and stored in a dry box purged with nitrogen and protected from light.

Biotin Chip dil#1 contained four 120 nL spots of biotinylated probe. 5'-Hydrazide-A18 probes with 3'-biotinTEG were diluted with 5'-Hydrazide, un-modified A18 probe to a constant final concentration of 100 nM in 0.1M Sodium Phosphate pH 7.8, 10% glycerol. The spots were immobilized to the chip's surface using a non-contact printer, and arranged in a vertical line with the lowest concentration at the top. Each spot corresponded to 110 pM, 330 pM, 1 nM, or 3 nM of biotinylated probe.

Biotin Chip dil#2 contained five 1000 nL spots of biotinylated probe that were arranged in an "X" pattern on a chip. 5'-Hydrazide-A18 probes with 3'-biotinTEG were diluted with 5'-Hydrazide, un-modified A18 probe to a constant final concentration of 100 nM in 0.1M Sodium Phosphate pH 7.8, 10% glycerol. The control spot of 100 nM un-labeled A18 was located in the center of the chip. Starting with the highest concentration in the upper left corner and then proceeding from the left to the right, the four remaining spots represented the concentrations of 300 pM, 60 pM, 12 pM, and 2.4 pM of biotinylated probe.

The MRSA Chip consisted of a chip with two columns of four spots arranged vertically. The left column are fiducial spots of dried latex particles to orient the viewer. The test spots contained probes that specifically recognize sequences in:
mec A gene to identify methicillin-resistance,
fem B gene for specific recognition of *S. aureus*
tuf gene for recognition of the *Staphylococcu* genus
A control probe to ensure the chemistry was performed properly.

Example 2

Testing Procedures for Polymer Detection and Standard Detection Chips

A) Biotin Chips
Polymer Enhanced Detection.
125 uL of Streptavidin was applied to the biotin chip at a concentration of 1 µg/mL in 1× Hyb buffer (i.e., 5×SSC, 0.1% SDS, and 0.1% Blockaid™) and incubated at room temperature for five minutes. The chip was then washed four times with wash A (i.e., 0.1×SSC and 0.1% SDS) and wash B (i.e., 0.1×SSC). The sample was then incubated with 125 uL of 1 µg/mL of the biotin polymer diluted into 1× Hyb buffer for five minutes at room temperature. The chip was washed four times with wash B. Poly(horse radish peroxidase)-Streptavidin ("pHSA") was diluted to 1 µg/ml in 1× Hyb buffer and 125 uL was added to the chip, for 10 minutes incubation at room temperature. The chip was washed 6 times with wash B, then each chip was incubated with tetramethylbenzidine (TMB) for 10 minutes, washed with water, dried, and analyzed.
Standard ELISA Detection.
An anti-biotin horse radish peroxidase (anti-biotin/HRP) conjugate was diluted to 1 µg/mL in 1× Hyb buffer. 125 uL of the diluted anti-biotin/HRP was added to the chip, and incubated at room temperature for 10 minutes. The chip was then washed 6 times with wash B. Finally, TMB was added to each chip. After 10 minutes of incubation, the chip was washed with water, dried, and analyzed.
B) MRSA Chip
Target sequences from the femA gene in *Staphylococcus aureus* were mixed in water with 20 nM each of two biotinylated detector probe sequences. Ten µL aliquots of the samples were heated to 95° C. for 3 minutes and then diluted into 90 µL of 1× Hyb buffer (i.e., 5×SSC, 0.1% SDS, and 0.5% Blockaid™) that had already been pre-warmed on the surface of the chip. The samples were incubated at 53° C. for 30 minutes and then washed with 4 washes each of wash A (0.1×SSC, 0.1% SDS) and wash B (0.1×SSC).
Polymer Detection.
For polymer enhanced detection, streptavidin was diluted to 1 µL/mL in 1× Hyb buffer and 125 uL was incubated on the chip for 5 minutes. The chips were washed 4 times with wash B. Next, a biotin dextran polymer was diluted to 1 µL/mL in 1× Hyb buffer and 125 uL was incubated on the chip at room temperature for 10 minutes. The chip was washed 6 times with wash B. Mouse monoclonal anti-biotin/HRP was diluted to 1 µg/mL in 1× Hyb and 125 uL was incubated on the chip for 10 minutes. Finally, each chip was incubated with 125 uL of TMB for 10 minutes, washed with water, dried, and analyzed.
Standard Detection.
Mouse monoclonal anti-biotin/HRP was diluted to 1 µg/mL in 1× Hyb and 125 uL was incubated on the chip for 10 minutes. The chip was washed six times with wash B. Then, 125 uL of a precipitable formulation of the substrate TMB was added to each chip and incubated at room temperature for 10 minutes.

Example 3

The following example describes a basic method for forming a capped enhanced detection system (cEDS) by acetylating biotinylated dextran polymers.
Methods.
A stock of 2 mg/ml of 500 kDa amino dextran (Molecular Probes; P/N D7144) and 5 mg/ml of 70 kDa amino dextran (Molecular Probes; P/N D1862) was prepared in water. NHS-LC-biotin (Pierce, P/N 21335) was dissolved to a concentration of 10 mM (5.56 mg/ml) in water immediately before use. Varying volumes of the dextran polymer were diluted into 0.1 M borate buffer, pH 8.5. Varying volumes of the NHS-LC-biotin stock were combined with said dextran polymer solutions. The reactions were incubated on a shaker for 3 hours at room temperature. Immediately before it was used, NHS-sulfo-acetate (Pierce, P/N 26777) was dissolved in water to form the concentration of 30 mM. An equal volume of diluted NHS-sulfo-acetate was added to an equal volume of NHS-LC-biotin for each reaction. The reactions were incubated with shaking for 3 hours at room temperature. The samples were purified on a PD-10 (Pharmacia) chromatography column.

Example 4

The following method describes use of hydrazone chemistry to conjugate hydrazide-biotin to an aldehyde-modified polymer.
5 mg of aldehyde dextran polymer (70 kDa, Pierce) was dissolved in water. 5 mg of biotin hydrazide (Pierce) was dissolved in 450 uL DMSO. 32 mg sodiumcyanoborohydride was dissolved in 0.5 mL PBS. 200 uL of the aldehyde dextran was mixed with 30-100 uL of biotin hydrazide (If reduction of bond is sought also add 200 uL sodium borohydride). PBS was added to bring the volume of the solution to 800 uL. The solution was then reacted overnight at room temperature with agitation. The solution was then purified over PD-10 column.

Example 5

This example describes a method for determining the extent of biotinylation for various enhanced detection system molecules. Levels of biotinylation were determined with a ([2-(4'-hydroxyazobenzene)] benzoic acid)("HABA") kit from Pierce. The HABA formed a HABA-avidin complex, and the biotin in the sample displaced the HABA, causing a change in absorbance when measured at 500 nM. Since the change in absorbance was directly proportional to the amount of biotin, this assay was used to determine the extent of biotinylation per molecule.
Methods.
The HABA-avidin mixture was equilibrated to room temperature. The spectrophotometer was blanked with 800 µl of PBS, pH 7.2. 100 µl of ddH$_2$O was, first, added to the HABA-avidin microtube and, second, pipetted into a cuvette containing PBS buffer. The absorbance at 500 nM (A500) for the HABA-avidin and PBS mixture was recorded as the absorption level for HABA-avidin. 100 µl of biotinylated HRP was added as a positive control to the HABA-avidin cuvette mix and recorded at A500 of HRP+. Steps 1-4 were repeated for each of the biotinylated samples. 100 µl of biotinylated sample was added to the HABA-avidin sample; the sample's level of absorption was then recorded. Absorbance is equal to or above 0.3 at steps 5 and 8, if not dilute sample and the A500 dilution was determined. At steps 5 and 8, if the absorption level was below 0.3 absorbance units, then the biotinylated sample was diluted, retested, and A500 was recorded.

The following chart shows the level of biotinylation that was obtained for various types of EDS.

TABLE 1

| EDS Type | mol biotin/amino | Backbone Type | Biotins Present | Available Biotin Sites |
|---|---|---|---|---|
| 3 × 70 kDa | 3 | 70 kDa Dextran | ~18 | 18 |
| 1/3 × 500 kDa | 0.3 | 500 kDa Dextran | 34 | 85 |
| 1 × 500 kDa | 1 | 500 kDa Dextran | 65 | 85 |
| 3 × 500 kDa | 3 | 500 kDa Dextran | ~85 | 85 |
| 3 × Chromalink | 3 | 500 kDa Dextran | 77.1 | 85 |
| 4% Acrylate | | Acrylate | 27 | 650 |
| 10% Acrylate | | Acrylate | 72 | 650 |
| Molecular Probes | NA | 500 kDa Dextran | 79 | 85 |

Example 6

Effect of Various EDS Formulations on Assay Sensitivity

A dilution series ranging from high concentration to low concentration (specifically, 1 pM, 100 fM, 33 fM, 11 fM, 3.75 fM, 1.25 fM, control) was tested on a chip containing model target DNA sequences from the femA gene in methicillin-resistant strains of *Staphylococcus aureus* ("MRSA"). A standard detection assay, which used an anti-biotin antibody conjugated to a horse radish peroxidase, was compared to a biotin polymer assay in 1× Hyb.

The standard assay on a thin film biosensor produced a visible signal at 1 pM but did not produce a visible signal at 100 fM. The LLOD for the standard detection approach was approximately 300 fM. The data for the 500 kD biotin polymer was a solid signal at 30 fM, a faint signal at 3.75 aM, and an even fainter signal at 1.25 fM. Therefore, the 500 kD biotin polymer improved the detection limit to a concentration within the range of 1.25 fM to 3.75 fM, which was an improvement of 80-240 fold in LLOD. The chart below outlines the performance for each of the EDS types tested as described:

TABLE 2

| EDS Type | Chip tested | Fold-enhancement over standard detection |
|---|---|---|
| 3 × 70 kDa | MRSA | 20-120 fold |
| 1/3 × 500 kDa | Biotin chip dil#2 | ~25 fold |
| 1 × 500 kDa | Biotin chip dil#2 | ~40 fold |
| 3 × 500 kDa | MRSA, biotin chip dil#1 | ~80 fold |
| 3 × 500 kDa | Biotin chip dil#1 | 80-240 fold |
| 3 × Chromalink | Biotin chip dil#1 | 80-240 fold |
| 4% Acrylate | Biotin chip dil#1 | 5-40 fold |
| 10% Acrylate | Biotin chip dil#1 | 5-40 fold |
| Molecular Probes | Biotin chip dil#1 | 3-10 fold |
| Molecular Probes | MRSA | ND |

The use of smaller polymers resulted in less than 2-4 fold intensity of detectable signal, as compared to the 500 kDa polymer. However, in theory the 70 kDa cEDS could work just as well since the 70 kDa cEDS could pack more densely and may have faster binding kinetics than the 500 kDa cEDS The effect of the number of biotin molecules conjugated per EDS was tested. The data showed that increasing the number of biotins from 34 to 65 then to 85 per backbone was roughly correlated with an improvement in LLOD. However, a second experiment that compared increasing number of biotins in the acrylate EDS polymers did not show the same correlation. The experimenters concluded that the type of polymer was important factor for obtaining an optimal signal enhancement. An experiment was performed comparing 3×500 kD dextran polymer (approximately 85 biotins) with the 10% acrylate (approximately 71 biotins). Even though the number of biotins was approximately the same, the dextran polymer was over 10 times as strong.

In theory, one could also use biotinylation reagents with appropriate linker length to prevent interference between the biotin on the polymer and strepavidin. Also, some linkers may provide for better performance based on properties such as flexibility or solubility. Several examples are NHS-LC-biotin (Pierce), NHS-LC-LC-biotin (Pierce), NHS-Chromalink (Solulink), NHS-PEGn-biotin (Nektar), and NHS-DNA probes.

The following experiment was designed to test the effect of linker type on biotinylation. Biotin polymers were created with NHS-LC-biotin (~85 biotins/polymer) and NHS-Chromalink (77 biotins/polymer) with approximately the same number of biotins/polymer. The chromalink conjugated polymers were compared to NHS-LC-biotin in Biotin chip dil#1. The data suggested that the polymers have appreciably the same activity for signal enhancement on the biotin chip and that the chemistry options with respect to linker type are numerous.

The cEDS reagent was compared to the 500 kDa biotin polymer from Molecular Probes on the Biotin chip dil#1. Under the normal test conditions, cEDS were at least 25-fold better than the biotin polymers made by Molecular Probes. The signal was apparent in all four dilutions with the polymer but it was very weak by the $3^{rd}$ dilution with the Molecular Probes polymer in hybridization buffer. Therefore, the GBS polymer, is at least 25-fold more sensitive than the Molecular Probe. (Both polymers had the same molecular weight and approximately the same number of biotins/polymers. GBS had 85 biotins/polymer and MP polymer had 79 biotins/polymer.

The cEDS and biotin dextran amplification polymer were compared on an MRSA chip. In this experiment, femA target sequences were tested as described. The data showed the cEDS can be clearly detected down to 1.25-3.75 fM, whereas the MP biotin dextran has significantly non-specific interactions with the chip surface, making detection of the specific probe untenable.

Example 7

Comparison of Capped (cEDS) and Uncapped (EDS) Biotin Dextran Polymers

In one experiment, the acylation of the remaining amino groups, with NHS-acetate, on the polymer after modification with NHS biotin, and subsequent purification on a size exclusion column improved signal enhancement. Signal enhancement, which was reproducible, was improved by at least 10-fold. Different fractions of 500 kDa biotin dextran polymer were tested on a Biotin chip dil#2, using the following methodology: a. biotinylated polymer untreated, b. biotinylated polymer acetylated with NHS-acetate, c. acetylated, biotinylated polymer passed over a PD10 column to remove excess NHS-acetate. The unacetylated gel and the acetylated gel showed spots of similar intensity at 12 pM, 300 pM, and 60 pM concentration of biotinylated probe. The results of the gel showed that simply acetylating the polymer had no effect on LLOD. After the acetylated polymer was passed over the PD10 column, signal was also detected at the 2.4 pM spot, which was approximately a ten to twenty fold improvement.

The acylation further served to mitigate nonspecific interactions of the polymers with the surface. In a test of the same series of polymers described on Biotin chip dil#2, the unacetylated fraction of the biotin polymer the results appeared sporadically, which is typical of non-specific binding. The sporadic results were most likely caused by the remaining unblocked amino groups on the dextran polymer as they interacted non-specifically with the surface of the chip. The results of the unacetylated gel showed spotting at the 300 pM and the 60 pM spots. The results of the acetylated gel show an additional faint spot at 12 pM ant 2.4 pM. The results of the PD10 purification were similar to the acylated results, except that the intensity of the spotting was increased at the 12 pM concentration. This observation likely accounted for the observation that the amplification polymer cannot be used with the assay enhancer PVP. The amplification polymer contains 147 free lysines that can contribute to non-specific interactions. In the following experiment, polymers were tested as described on Biotin chip dil#1. The results of the experiment were that PVP enhanced the performance of the GBS polymer ~3-fold, whereas it created a surface passivation with the amplification polymer. Amplification polymers having greater solubility in buffers at basic pH were found to perform better.

The samples that contained GBS amplification polymer, biotin, dextran, and hybridization buffer gave off a medium-level signal. Exchanging the buffer for buffer 2% PVP resulted in an increase of signal at all 4 spots. The sample that contained the commercially obtained amplification (Molecular Probes) polymer, biotin, dextran, and hybridization buffer only produced signal at 1 nM and 3 nM, with a very faint signal at 330 pM.

Example 9

The addition of large water soluble polymers such as polyvinyl pyrrolidone (PVP) and polyethylene glycol (PEG) enhance signaled an additional 2-4 fold when used in conjunction with cEDS. This was not likely due to general improvement in detection of surface-immobilized biotin because direct detection of the primary biotin with anti-biotin/HRP and TMB is not effected. Overall enhancements for detecting surface-immobilized biotin were improved to 160 to 480-fold.

The addition of 0.5% PVP to a femA gene detection assay buffer enhanced signal. A dilution series of model target sequences from the femA gene in *Staphylococcus aureus* was tested on the MRSA chip to determine the effect of cEDS on the LLOD. The PVP was added to the 1× Hyb buffer used to dilute cEDS and the polyHRP/SA. The results were that polymers alone improved the LLOD by 80 to 240 fold. Addition of 0.5% PVP and polymer improved the LLOD to 160 to 480 fold.

The addition of a non-ionic polymer compound during the cEDS incubation step improved signal enhancement by ~3-fold compared to cEDS incubated without the compound. Other non-ionic polymer_compounds may enhance signal also. Addition of 2% polyvinyl pyrrolidone (PVP) 40 kD, or 1-2% polyethylene glycol (PEG) 8 kD to the 1× Hyb buffer for the cEDS and polyHRP/SA incubations improved signal enhancement by an additional 3-fold above that of cEDS alone.

Several other non-ionic polymer compounds may also work to enhance the performance of the cEDS system. The following table summarizes data from the testing of various polymeric buffer additives on Biotin chip dil#1. Polyvinyl-X polymers with X=pyrollidone, sulfate, or carboxylate worked roughly equivalently at >40 kDa molecular weight. Polyethylene glycol in the range of 8-40 kDa were close in efficacy to 40 kDa polyvinyl pyrrolidone. Larger molecular weight dextran sulfate and low percentages of carboxy methyl cellulose also had a measurable effect on enhancing cEDS performance. Interestingly, alcohol and stearate side groups on polyvinyl backbones did not enhance the performance of the cEDS reagents.

TABLE 3

| Buffer Additive | Molecular Weight | Useful Range | Fold-Enhance EDS |
|---|---|---|---|
| Dextran sulfate | 5 kD | 0.5-3% | None |
| Dextran sulfate | 12 kD | 0.5-2% | None |
| Dextran sulfate | 500 kD | 0.5-2% | 2-4* |
| Amino dextran | 70 kD | 0.5-3% | 2-4 |
| Polyvinyl pyrollidone | 10 kD | 0.5-3% | None |
| Polyvinyl pyrollidone | 40 kD | 0.5-2% | 2-4* |
| Polyvinyl sulfate | 170 kD | 0.5-1% | 2-4* |
| Polyvinyl stearate | 90 kD | 0.5-3% | None |
| Polyvinyl alcohol | 40 kD | 0.1-1% | None |
| Polyethylene glycol | 8 kD | | 2-4 |
| Polyethylene glycol | 40 kD | 0.5-2% | 2-10* |
| Carboxymethyl cellulose | | 0.05-0.36% | 2-4* |
| Polyacrylic acid | 100 kD | 0.5% | 2-4* |
| Polyacrylic acid | 250 kD | 0.5% | 2-4* |

*Indicates that significant surface passivation occurs at higher concentrations

Additional experiments indicated that addition of PVP had no general effect on assay performance. The first sample contained 1× Hyb buffer was used to dilute the anti-biotin/HRP complex, and the second sample was the same as the first sample (except that it also contained PVP) was compared with the same sample and compared with no added PVP in testing on the Biotin chip dil#2. No signal enhancement was observed with the addition of up to 4% PVP in the general assay, indicating that the effect is specific to enhanced cEDS reagent performance.

It is to be understood that the foregoing descriptions of embodiments of the present invention are exemplary and explanatory only, are not restrictive of the invention, as claimed, and merely illustrate various embodiments of the invention. It will be appreciated that other particular embodiments consistent with the principles described in the specification but not expressly disclosed may fall within the scope of the claims.

What is claimed is:

1. A method for performing a diagnostic assay, comprising:
   providing an amplification polymer, the polymer further comprising:
   a plurality of amine groups;
   a plurality of detectable labels conjugated to a portion of the amine groups;
   a plurality of amine capping groups conjugated to a portion of the plurality of amine groups not conjugated to the detectable labels;
   wherein the amplification polymer is neutrally charged and soluble in water; and
   contacting the amplification polymer with a sample suspected of having an analyte.

2. The method claim 1, wherein the polymer is selected from the group consisting of: amino dextran, poly-L-lysine, poly(Arg,Trp), and poly(Lys,Phe).

3. The method of claim 1, wherein the polymer is amino dextran.

4. The method of claim 1, wherein the plurality of amine capping groups conjugated to the portion of the plurality of amine groups not conjugated to the detectable labels are derived from reacting the plurality of amine groups with a capping reagent selected from the group consisting of: succinimidyl esters, diazoacetates, imidoesters, carbodimides, maleimides, α-haloacetyls, aryl halides, dicarbonyl compounds, and hydrazides.

5. The method of claim 1, wherein the plurality of amine capping groups conjugated to the portion of the plurality of amine groups not conjugated to the detectable labels are derived from reacting the plurality of amine groups with a capping reagent selected from the group consisting of: N-ethylmaleimide, NHS-acetate, iodoacetic acid, N-[iodoethyl] (trifluoroacetamide), 3,4-difluoronitro-benzene (DFNB), sulfonyl halide, (ammonium 4-chloro-7-sulfobenzo-furazan)-chloride (SBF-chloride), glyoxal, phenyglyoxal, 2,3-butanedione, and 1,2-cyclohexane-dione.

6. The method of claim 1, wherein the plurality of amine capping groups is acetyl.

7. The method of claim 3, wherein the plurality of amine capping groups is acetyl.

8. The method of claim 1, wherein the detectable label complexes are each biotin.

9. The method of claim 3, wherein the detectable label complexes are each biotin.

10. The method of claim 6, wherein the detectable label complexes are each biotin.

11. The method of claim 7, wherein the detectable label complexes are each biotin.

12. A method of preparing an amplification polymer for use in a diagnostic assay, comprising:
providing a polymer having a plurality of amine groups;
conjugating a plurality of detectable labels to a portion of the amine groups;
capping a portion of the amine groups not conjugated to the detectable labels with an amine capping reagent;
wherein the amplification polymer is neutrally charged and soluble in water.

13. The method claim 12, wherein the polymer is selected from the group consisting of: amino dextran, poly-L-lysine, poly(Arg,Trp), and poly(Lys,Phe).

14. The method of claim 12, wherein the polymer is amino dextran.

15. The method of claim 12, wherein the plurality of amine capping groups conjugated to the portion of the plurality of amine groups not conjugated to the detectable labels are derived from reacting the plurality of amine groups with a capping reagent selected from the group consisting of: succinimidyl esters, diazoacetates, imidoesters, carbodimides, maleimides, α-haloacetyls, aryl halides, dicarbonyl compounds, and hydrazides.

16. The method of claim 12, wherein the plurality of amine capping groups conjugated to the portion of the plurality of amine groups not conjugated to the detectable labels are derived from reacting the plurality of amine groups with a capping reagent selected from the group consisting of: N-ethylmaleimide, NHS-acetate, iodoacetic acid, N-[iodoethyl] (trifluoroacetamide), 3,4-difluoronitro-benzene (DFNB), sulfonyl halide, (ammonium 4-chloro-7-sulfobenzo-furazan)-chloride (SBF-chloride), glyoxal, phenyglyoxal, 2,3-butanedione, and 1,2-cyclohexane-dione.

17. The method of claim 12, wherein the plurality of amine capping groups is acetyl.

18. The method of claim 15, wherein the plurality of amine capping groups is acetyl.

19. The method of claim 12, wherein the detectable label complexes are each biotin.

20. The method of claim 15, wherein the detectable label complexes are each biotin.

21. The method of claim 18, wherein the detectable label complexes are each biotin.

22. The method of claim 19, wherein the detectable label complexes are each biotin.

* * * * *